US012733894B2

(12) United States Patent
Iwashita et al.

(10) Patent No.: US 12,733,894 B2
(45) Date of Patent: Sep. 15, 2026

(54) IMAGE PROCESSING APPARATUS, RADIATION IMAGING SYSTEM, IMAGE PROCESSING METHOD, AND STORAGE MEDIUM

(71) Applicant: CANON KABUSHIKI KAISHA, Tokyo (JP)

(72) Inventors: Atsushi Iwashita, Tokyo (JP); Kosuke Terui, Kanagawa (JP); Ryuichi Fujimoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 171 days.

(21) Appl. No.: 18/650,625

(22) Filed: Apr. 30, 2024

(65) Prior Publication Data

US 2025/0003895 A1 Jan. 2, 2025

(30) Foreign Application Priority Data

Jun. 29, 2023 (JP) ................................. 2023-107226

(51) Int. Cl.
*A61B 6/00* (2024.01)
*A61B 6/42* (2024.01)

(52) U.S. Cl.
CPC .......... *A61B 6/5282* (2013.01); *A61B 6/4233* (2013.01); *A61B 6/482* (2013.01); *A61B 6/487* (2013.01)

(58) Field of Classification Search
CPC ............. G01N 23/20083; G01N 23/04; G01N 23/083; G01N 2223/401; G01N 2223/6123; G01N 2223/6126; G01N 2223/633
See application file for complete search history.

(56) References Cited

U.S. PATENT DOCUMENTS

| | | | |
|---|---|---|---|
| 9,048,154 | B2 | 6/2015 | Takenaka |
| 9,128,196 | B2 | 9/2015 | Sato |
| 9,134,432 | B2 | 9/2015 | Iwashita |
| 9,234,966 | B2 | 1/2016 | Sugawara |
| 9,423,512 | B2 | 8/2016 | Sato |
| 9,445,030 | B2 | 9/2016 | Yagi |
| 9,462,989 | B2 | 10/2016 | Takenaka |
| 9,468,414 | B2 | 10/2016 | Ryu |
| 9,470,800 | B2 | 10/2016 | Iwashita |
| 9,470,802 | B2 | 10/2016 | Okada |
| 9,541,653 | B2 | 1/2017 | Iwashita |

(Continued)

FOREIGN PATENT DOCUMENTS

| | | |
|---|---|---|
| JP | 2008-167948 A | 7/2008 |
| JP | 2019-166155 A | 10/2019 |

*Primary Examiner* — Uzma Alam
*Assistant Examiner* — Mamadou Faye
(74) *Attorney, Agent, or Firm* — VENABLE LLP

(57) ABSTRACT

An image processing apparatus includes a processing unit configured to, by using a plurality of pieces of information that correspond to a plurality of mutually different radiation energies and that have been obtained by irradiating an object with radiation and performing imaging, and information regarding transmittance including scattered rays and transmittance not including the scattered rays that is set in advance for each of multiple thicknesses of a first material and a second material that is different from the first material, obtain thickness images of the first and second materials in which the scattered rays have been corrected.

15 Claims, 10 Drawing Sheets

(56) References Cited

U.S. PATENT DOCUMENTS 9,655,586 B2 5/2017 Yagi
9,737,271 B2 8/2017 Iwashita
9,812,474 B2 11/2017 Yagi
9,971,046 B2 5/2018 Ryu
9,989,656 B2 6/2018 Sato
10,009,990 B2 6/2018 Takenaka
10,197,684 B2 2/2019 Terui
10,274,612 B2 4/2019 Ishii
10,441,238 B2 10/2019 Terui
10,779,777 B2 9/2020 Terui
10,782,251 B2 9/2020 Sato
11,047,808 B2 6/2021 Iwashita
11,047,994 B2 6/2021 Terui
11,185,301 B2 11/2021 Torii
11,187,816 B2 11/2021 Takenaka
11,252,349 B2 2/2022 Kosuge
11,280,919 B2 3/2022 Takenaka
11,303,831 B2 4/2022 Iwashita
11,360,034 B2 6/2022 Torii
11,430,161 B2 8/2022 Iwashita
11,531,122 B2 12/2022 Terui
RE49,401 E 1/2023 Iwashita
11,635,392 B2 4/2023 Noda
11,686,691 B2 6/2023 Iwashita
11,813,095 B2 11/2023 Torii
2005/0058242 A1* 3/2005 Peschmann .............. G01V 5/22 378/57
2009/0010386 A1* 1/2009 Peschmann ............ G01N 23/20 378/57
2019/0290234 A1 9/2019 Kuwabara
2021/0244374 A1* 8/2021 Zhao .................... A61B 6/4007
2021/0307714 A1* 10/2021 Scott ......................... G06T 5/70
2022/0120919 A1 4/2022 Terui
2022/0167935 A1 6/2022 Iwashita
2022/0249049 A1* 8/2022 Kawamura ............ A61B 6/583
2022/0323032 A1* 10/2022 Kawamura .......... G06N 3/0464
2023/0017704 A1* 1/2023 Taki ..................... A61B 6/5217
2024/0053497 A1 2/2024 Takasaki

* cited by examiner 20
202
203
201
204
204a
204b
204c
204'
204'a
204'b
205
205a
205b
205'a
205'b
206
206a
206b
206c
206d
206e
207
207S
207Sa
207Sb
207N
207Na
207Nb
208
208S
208Sa
208Sb
208N
208Na
208Nb
209
209S
209N
21
21S
21N
Vres
PRES
EN
ENn
EN0
PCL
VCL
TS
TN
ADD
S Hold
N Hold
VSR
INVERT CAP(P)
X5.5
X24.5
WIDE
WIDE2
S
N

FIG. 3

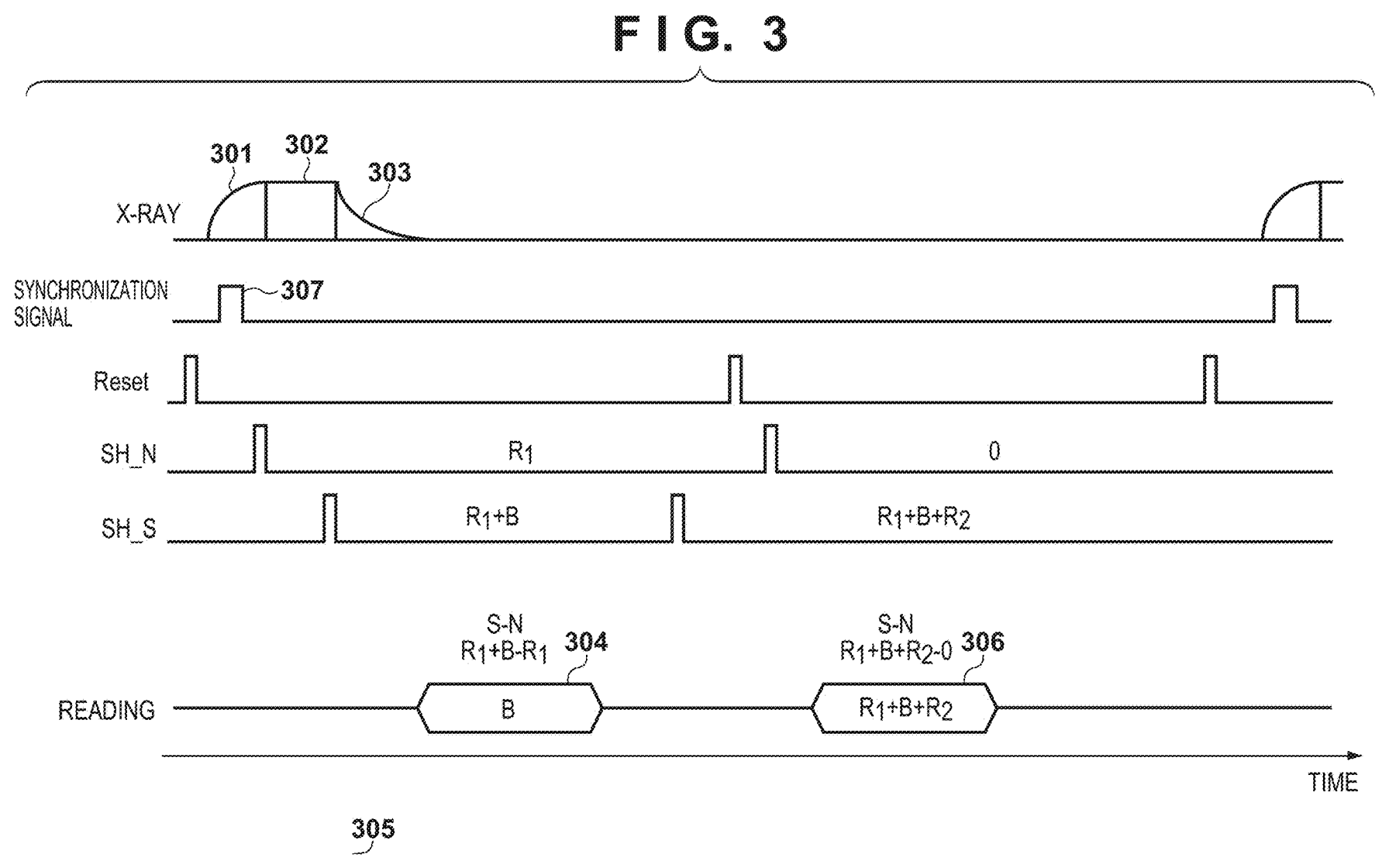

X-RAY
SYNCHRONIZATION SIGNAL
Reset
SH_N
SH_S
READING
TIME
301
302
303
307
$R_1$
$R_1+B$
S-N
$R_1+B-R_1$
B
304
0
$R_1+B+R_2$
S-N
$R_1+B+R_2-0$
$R_1+B+R_2$
306
305 l
0 1 2 3 ... M-1
0 1 2 3 ... M-1
h
l'=L*M
h'=H*M
BONE THICKNESS TABLE B[1,h]
SOFT TISSUE THICKNESS TABLE S[1,h]

901

| n | S[n] | $H_{real}[n]$ | $H_{ideal}[n]$ |
|---|---|---|---|
| 0 | 0 | 1 | 1 |
| 1 | 5 | 0.322348 | 0.300100 |
| 2 | 10 | 0.115458 | 0.091504 |
| 3 | 15 | 0.043388 | 0.028213 |
| 4 | 20 | 0.016151 | 0.008779 |
| 5 | 25 | 0.006403 | 0.002687 |

902

| n | S[n] | $L_{real}[n]$ | $L_{ideal}[n]$ |
|---|---|---|---|
| 0 | 0 | 1 | 1 |
| 1 | 5 | 0.238206 | 0.234323 |
| 2 | 10 | 0.065029 | 0.057639 |
| 3 | 15 | 0.018948 | 0.014585 |
| 4 | 20 | 0.005499 | 0.003763 |
| 5 | 25 | 0.001738 | 0.000932 |

| $H_{real}[m,n]$ | | B[m] | | | |
|---|---|---|---|---|---|
| | | 0 | 1 | 2 | 3 |
| S[n] | 0 | 1 | 0.422077 | 0.210254 | 0.112591 |
| | 5 | 0.322348 | 0.14922 | 0.078075 | 0.04296 |
| | 10 | 0.115458 | 0.056666 | 0.029853 | 0.01672 |
| | 15 | 0.043388 | 0.021575 | 0.011896 | 0.006724 |
| | 20 | 0.016151 | 0.008403 | 0.004589 | 0.002622 |
| | 25 | 0.006403 | 0.003374 | 0.001863 | 0.001075 |

1102

| $L_{real}[m,n]$ | | B[m] | | | |
|---|---|---|---|---|---|
| | | 0 | 1 | 2 | 3 |
| S[n] | 0 | 1 | 0.203139 | 0.060302 | 0.021124 |
| | 5 | 0.238206 | 0.05649 | 0.018109 | 0.006686 |
| | 10 | 0.065029 | 0.017204 | 0.005665 | 0.002171 |
| | 15 | 0.018948 | 0.00528 | 0.001899 | 0.000752 |
| | 20 | 0.005499 | 0.001682 | 0.000598 | 0.000289 |
| | 25 | 0.001738 | 0.000548 | 0.000257 | 0.000169 |

IMAGE PROCESSING APPARATUS, RADIATION IMAGING SYSTEM, IMAGE PROCESSING METHOD, AND STORAGE MEDIUM

BACKGROUND OF THE INVENTION

Field of the Invention

The technique disclosed herein relates to an image processing apparatus, a radiation imaging system, an image processing method, and a storage medium. Specifically, the technique disclosed herein relates to an image processing apparatus, a radiation imaging system, an image processing method, and a storage medium to be used in medical diagnosis for the capturing of still images, such as general radiography, and for the capturing of moving images, such as fluoroscopy.

Description of the Related Art

Currently, radiation imaging apparatuses in which a flat panel detector (hereinafter "FPD") formed from a semiconductor material is used are being widely used as imaging apparatuses for use in X-ray-based medical imaging diagnosis and non-destructive examination.

In energy subtraction, which is an imaging method in which an FPD is used, material decomposition images, such as a bone image and a soft tissue image for example, can be obtained by processing a plurality of images of different energies obtained by emitting X-rays with different tube voltages (Japanese Patent Laid-Open No. 2008-167948).

Japanese Patent Laid-Open No. 2019-166155 discloses a technique in which scattered ray correction is performed in order to reduce errors occurring in bone and soft tissue thickness when a bone image and a soft tissue image are generated using energy subtraction.

The scattered ray dose needs to be estimated in order to perform scattered ray correction; however, because the scattered ray dose differs for different materials constituting an object, errors in bone and soft tissue thickness may occur if correction is performed without taking the materials into consideration.

The technique disclosed herein provides an image processing technique with which the thickness of materials can be obtained accurately.

SUMMARY OF THE INVENTION

According to one aspect of the present invention, there is provided an image processing apparatus comprising a processing unit configured to, by using a plurality of pieces of information that correspond to a plurality of mutually different radiation energies and that have been obtained by irradiating an object with radiation and performing imaging, and information regarding transmittance including scattered rays and transmittance not including the scattered rays that is set in advance for each of multiple thicknesses of a first material and a second material that is different from the first material, obtain thickness images of the first and second materials in which the scattered rays have been corrected.

BRIEF DESCRIPTION OF THE DRAWINGS

FIG. 3 is a timing chart of the X-ray imaging apparatus according to the embodiment.

FIG. 11 is a diagram illustrating tables for scattered ray correction in which two materials are taken into consideration according to the embodiment.

DESCRIPTION OF THE EMBODIMENTS

Figure 1:
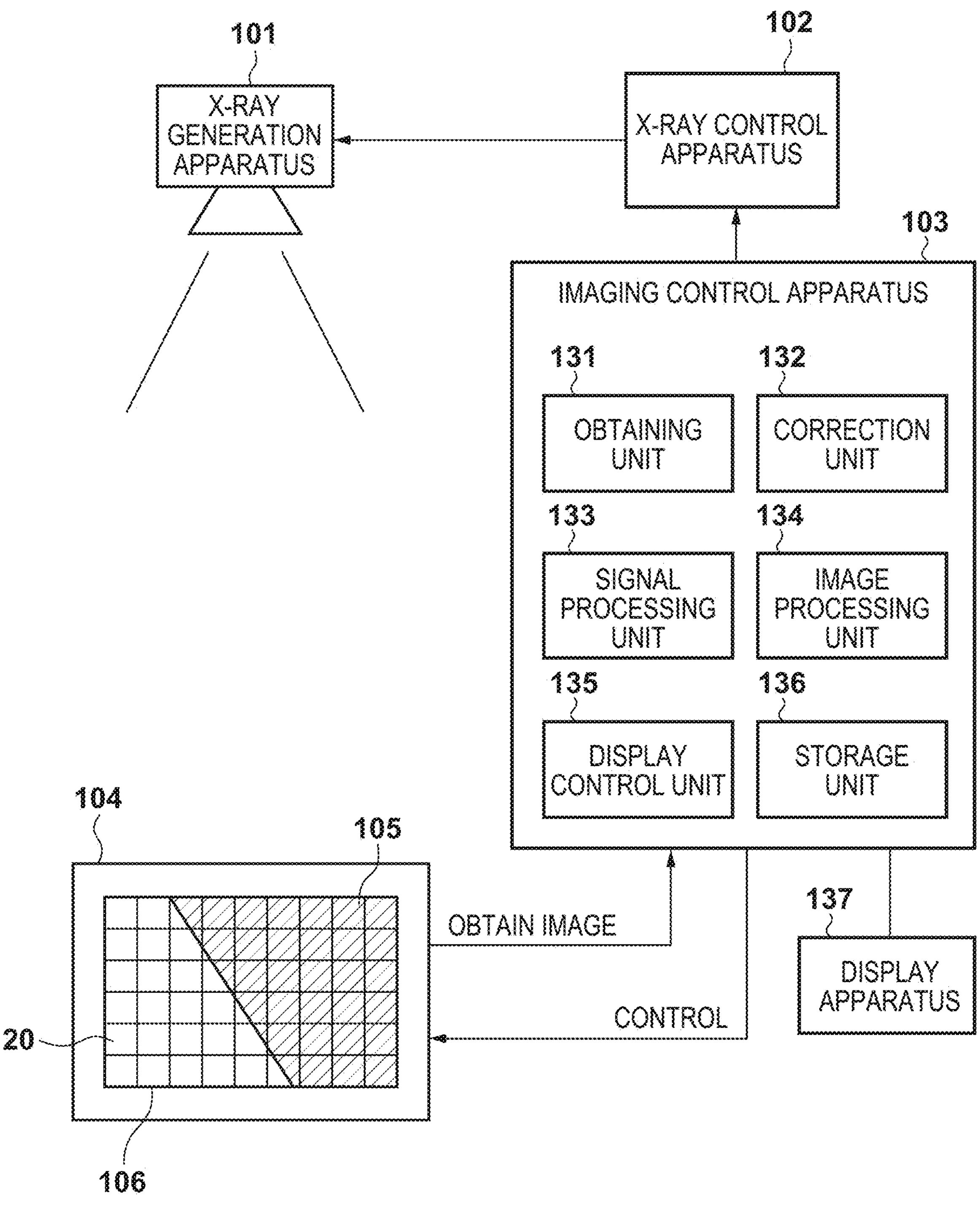
FIG. 1 is a diagram illustrating an example of a configuration of an X-ray imaging system according to an embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Note that the term "radiation" in the technique disclosed herein includes, in addition to alpha rays, beta rays, gamma rays, etc., which are beams formed by particles (including photons) that are emitted as a result of radioactive decay, beams having similar or higher energies, such as X-rays, particle beams, and cosmic rays. In the following embodiment, an apparatus in which X-rays are used as one example of radiation will be described. Accordingly, in the following, an X-ray imaging apparatus and an X-ray imaging system will be described as a radiation imaging apparatus and a radiation imaging system, respectively.

Embodiment

FIG. 1 is a block diagram illustrating an example of a configuration of an X-ray imaging system that is an example of a radiation imaging system according to the embodiment. The X-ray imaging system according to the embodiment includes an X-ray generation apparatus 101 (radiation source), an X-ray control apparatus 102, an imaging control apparatus 103, and an X-ray imaging apparatus 104 (radiation imaging apparatus). The radiation imaging system includes the X-ray imaging apparatus 104 (radiation imaging apparatus), which includes a two-dimensional detector 106, and the imaging control apparatus 103 (image processing apparatus), which obtains images in which scattered rays included in radiation detected by the two-dimensional detector 106 have been corrected.

The X-ray generation apparatus 101 generates X-rays and irradiates an object with X-rays. The X-ray control apparatus 102 controls the generation of X-rays by the X-ray generation apparatus 101. The imaging control apparatus 103 includes at least one processor (CPU) and a memory (storage unit 136), for example, and obtains X-ray images and performs image processing as a result of the processor executing one or more programs stored in the memory (storage unit 136). Note that the processing performed by the imaging control apparatus 103, which includes image processing, may be realized by dedicated hardware or by hardware and software working together. The X-ray imaging apparatus 104 includes a phosphor 105 that converts X-rays into visible light, and the two-dimensional detector 106, which detects visible light. The two-dimensional detector 106 is a sensor in which pixels 20 for detecting X-ray quanta are arranged in an array having X columns and Y rows, and outputs image information.

The imaging control apparatus 103 functions as an image processing apparatus that processes radiation images by means of the above-mentioned processor. An obtaining unit 131, a correction unit 132, a signal processing unit 133, an image processing unit 134, a display control unit 135, and the storage unit 136 indicate examples of functional configurations of the image processing apparatus.

The obtaining unit 131 obtains a plurality of radiation images of mutually different energies that have been obtained by irradiating an object with radiation and performing imaging. As the plurality of radiation images, the obtaining unit 131 obtains radiation images that have been obtained by performing sampling and holding multiple times during exposure to one shot of radiation.

The correction unit 132 corrects the plurality of radiation images obtained by the obtaining unit 131 and generates a plurality of images to be used in energy subtraction processing.

The signal processing unit 133, by using a plurality of pieces of information that correspond to a plurality of mutually different radiation energies and that have been obtained by irradiating an object with radiation and performing imaging, and information regarding transmittance including scattered rays and transmittance not including scattered rays that is set in advance for each of multiple thicknesses of a first material and a second material that is different from the first material, obtains thickness images of the first and second materials in which the scattered rays have been corrected.

Here, information that corresponds to a first radiation energy among the plurality of radiation energies and information that corresponds to a second radiation energy, among the plurality of radiation energies, that is different from the first radiation energy are included in the plurality of pieces of information. A first radiation image is included in the information that corresponds to the first radiation energy, and a second radiation image is included in the information that corresponds to the second radiation energy.

The first radiation image captured by the X-ray imaging apparatus 104 includes data in which signal values (pixel values) of electric signals (image signal) obtained by the imaging and position information indicating a two-dimensional array of the signal values are associated with one another. Furthermore, the second radiation image captured by the X-ray imaging apparatus 104 includes data in which signal values (pixel values) of electric signals (image signal) obtained by the imaging and position information indicating a two-dimensional array of the signal values are associated with one another. For example, the plurality of images (the first radiation image and the second radiation image) include images (material decomposition images) that represent materials in a state in which the materials are separated from one another (e.g., bone and soft tissue are separated from one another).

For example, the signal processing unit 133 generates a first image indicating a thickness of the first material and a second image indicating a thickness of the second material, which is different from the first material, based on the plurality of radiation images captured at the mutually different radiation energies. Here, at least calcium, hydroxyapatite, or bone is included in the first material, and at least water, fat, or a soft material that does not contain calcium is included in the second material. The signal processing unit 133 will be described in detail later. The image processing unit 134 generates display images using the first and second images obtained as a result of the signal processing by the signal processing unit 133. The display control unit 135 displays the thickness image of the first material and the thickness image of the second material obtained by the signal processing unit 133 on a display apparatus 137 that is formed from a liquid-crystal display, an organic EL display, or the like, for example.

The storage unit 136 stores various programs and databases (data tables), and the at least one processor (CPU) realizes the functions of the obtaining unit 131, the correction unit 132, the signal processing unit 133, the image processing unit 134, and the display control unit 135 by executing one or more programs stored in the storage unit 136.

Figure 2:
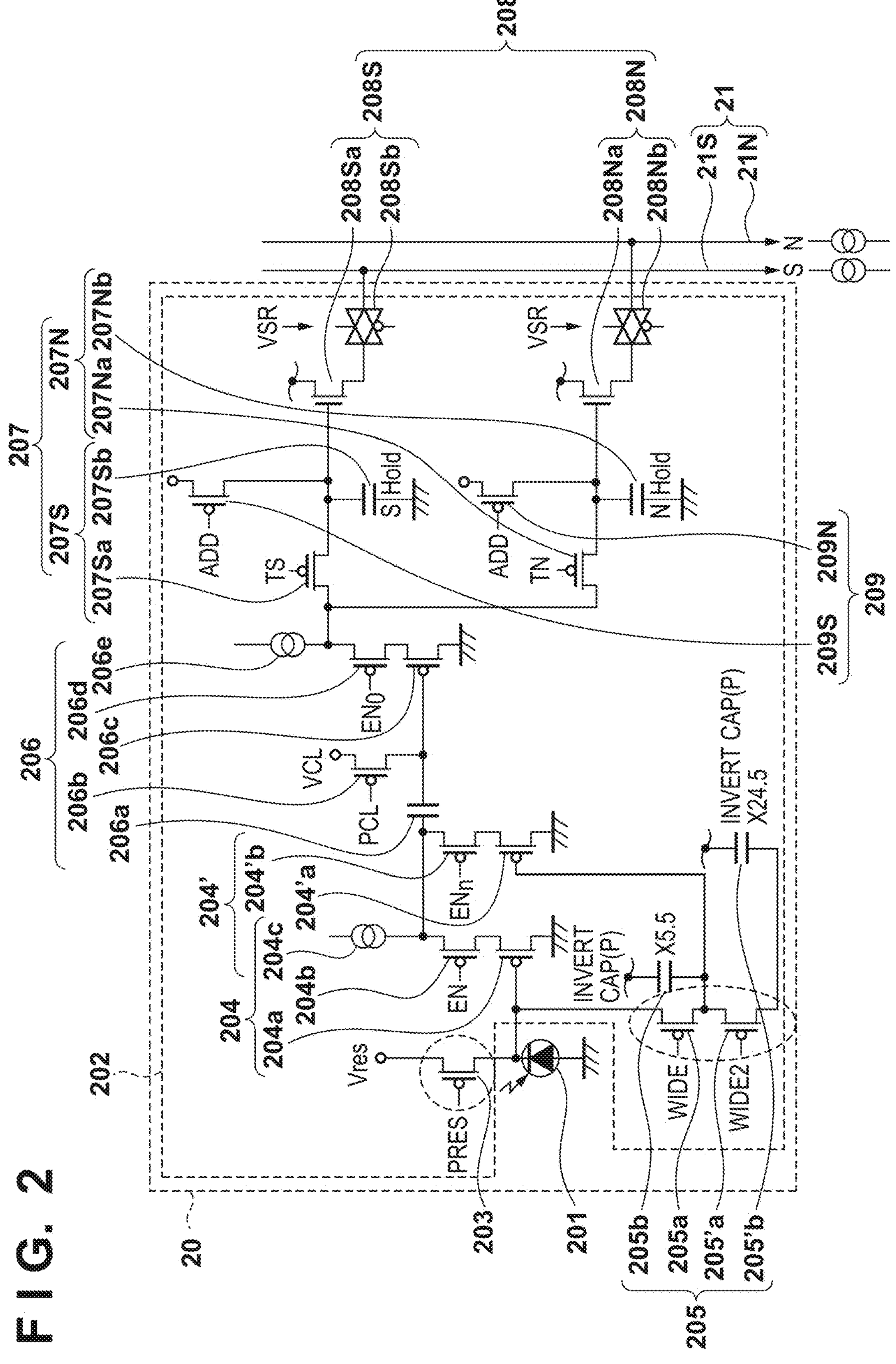
FIG. 2 is an equivalent circuit diagram of a pixel of an X-ray imaging apparatus according to the embodiment.

FIG. 2 is an equivalent circuit diagram of a pixel 20 according to the embodiment. The pixel 20 includes a photoelectric conversion element 201 and an output circuit section 202. The photoelectric conversion element 201 may typically be a photodiode. The output circuit section 202 includes an amplifier circuit section 204, a clamp circuit section 206, a sample-and-hold circuit section 207, and a selector circuit section 208.

The photoelectric conversion element 201 includes a charge accumulator, and the charge accumulator is connected to the gate of a MOS transistor **204*a* of the amplifier circuit section 204. The source of the MOS transistor 204*a* is connected to a current source 204*c* via a MOS transistor 204*b*. A source follower circuit is formed by the MOS transistor 204*a* and the current source 204*c*. The MOS transistor 204*b* is an enabling switch that switches on and puts the source follower circuit in an operating state when an enable signal EN supplied to the gate of the MOS transistor 204*b*** is set to an active level.

In the example illustrated in FIG. 2, the charge accumulator of the photoelectric conversion element 201 and the gate of the MOS transistor **204*a* form one same node, and this node functions as a charge-voltage converter that converts charge accumulated in the charge accumulator into a voltage. That is, a voltage V (=Q/C) that is determined by the charge Q accumulated in the charge accumulator and a capacitance value C of the charge-voltage converter appears in the charge-voltage converter. The charge-voltage converter is connected to a reset potential Vres via a reset switch 203. When a reset signal PRES is set to an active level, the reset switch 203** switches on, and the potential of the charge-voltage converter is reset to the reset potential Vres.

The clamp circuit section 206 uses a clamp capacitor **206*a* and clamps noise that is output by the amplifier circuit section 204 in accordance with the reset potential of the charge-voltage converter. That is, the clamp circuit section 206 is a circuit for cancelling out this noise from a signal output from the source follower circuit in accordance with the charge generated by the photoelectric conversion element 201 through photoelectric conversion. This noise includes kTC noise generated when resetting is performed. The clamping is performed by setting a clamp signal PCL to an active level and switching a MOS transistor 206***b* on, and then setting the clamp signal PCL to a non-active level and switching the MOS transistor 206*b* off. The output side of the clamp capacitor 206*a* is connected to the gate of a MOS transistor 206*c*. The source of the MOS transistor 206*c* is connected to a current source 206*e* via a MOS transistor 206*d*. A source follower circuit is formed by the MOS transistor 206*c* and the current source 206*e*. The MOS transistor 206*d* is an enabling switch that switches on and puts the source follower circuit in an operating state when an enable signal EN0 supplied to the gate of the MOS transistor 206*d* is set to an active level.

The signal that is output from the clamp circuit section 206 in accordance with the charge generated by the photoelectric conversion element 201 through photoelectric conversion is written as a light signal to a capacitor 207Sb via a switch 207Sa when a light-signal sampling signal TS is set to an active level. A signal that is output from the clamp circuit section 206 when the MOS transistor 206*b* is switched on immediately after the potential of the charge-voltage converter is reset is a clamp voltage. The noise signal is written to a capacitor 207Nb via a switch 207Na when a noise sampling signal TN is set to an active level. This noise signal includes an offset component of the clamp circuit section 206. A signal sample-and-hold circuit 207S is formed by the switch 207Sa and the capacitor 207Sb, and a noise sample-and-hold circuit 207N is formed by the switch 207Na and the capacitor 207Nb. The sample-and-hold circuit section 207 includes the signal sample-and-hold circuit 207S and the noise sample-and-hold circuit 207N.

When a driving circuit section drives and sets a row selection signal to an active level, the signal (light signal) held in the capacitor 207Sb is output to a signal line 21S via a MOS transistor 208Sa and a row selection switch 208Sb. Furthermore, the signal (noise) held in the capacitor 207Nb is simultaneously output to a signal line 21N via a MOS transistor 208Na and a row selection switch 208Nb. The MOS transistor 208Sa, along with a constant current source (unillustrated) provided to the signal line 21S, forms a source follower circuit. Similarly, the MOS transistor 208Na, along with a constant current source (not illustrated) provided to the signal line 21N, forms a source follower circuit. A signal selector circuit section 208S is formed by the MOS transistor 208Sa and the row selection switch 208Sb, and a noise selector circuit section 208N is formed by the MOS transistor 208Na and the row selection switch 208Nb. The selector circuit section 208 includes the signal selector circuit section 208S and the noise selector circuit section 208N.

The pixel 20 may include an adding switch 209S for adding light signals of a plurality of adjacent pixels 20. During an adding mode, an adding mode signal ADD is set to an active level, and the adding switch 209S is switched on. Thus, the capacitors 207Sb of adjacent pixels 20 are mutually connected by the adding switch 209S, and the light signals are averaged. Similarly, the pixel 20 may include an adding switch 209N for adding noises of a plurality of adjacent pixels 20. When the adding switch 209N switches on, the capacitors 207Nb of adjacent pixels 20 are mutually connected by the adding switch 209N, and the noises are averaged. An adding section 209 includes the adding switch 209S and the adding switch 209N.

Furthermore, the pixel 20 may include a sensitivity changing section 205 for changing sensitivity. For example, the pixel 20 may include a first sensitivity changing switch 205*a* and a second sensitivity changing switch 205'*a*, and circuit elements accompanying these switches. When a first change signal WIDE is set to an active level, the first sensitivity changing switch 205*a* switches on, and the capacitance value of a first additional capacitor 205*b* is added to the capacitance value of the charge-voltage converter. Thus, the sensitivity of the pixel 20 decreases. When a second change signal WIDE2 is set to an active level, the second sensitivity changing switch 205'*a* switches on, and the capacitance value of a second additional capacitor 205'*b* is added to the capacitance value of the charge-voltage converter. Thus, the sensitivity of the pixel 20 decreases to a further extent. By adding a function of decreasing the sensitivity of the pixel 20 in such manner, the pixel 20 can receive a larger light amount and the dynamic range thereof can be widened. If the first change signal WIDE is set to an active level, an enable signal ENn may be set to an active level to cause a MOS transistor 204'*a* to perform a source follower operation in place of the MOS transistor 204*a*.

The X-ray imaging apparatus 104 reads, from the two-dimensional detector 106, the output from the above-described pixel circuit, converts the output into a digital value using an AD converter (unillustrated), and then transfers an image to the imaging control apparatus 103.

Next, the operation of the X-ray imaging system according to the embodiment having the above-described configuration will be described. FIG. 3 illustrates driving timings of the X-ray imaging apparatus 104 when energy subtraction is performed in the X-ray imaging system according to the embodiment. With the horizontal axis indicating time, the waveforms in FIG. 3 indicate: X-ray exposure; a synchronization signal; the resetting of the photoelectric conversion element 201; the sample-and-hold circuit 207; and timings when images are read from the signal lines 21.

X-ray exposure is performed after the photoelectric conversion element 201 is reset by means of the reset signal. The X-ray tube voltage is ideally a square wave; however, it takes a finite amount of time for the tube voltage to rise and fall. Especially in a case in which a pulse X-ray beam is used and the exposure time is short, the tube voltage can no longer be regarded as a square wave, and exhibits a waveform as indicated by X-rays 301 to 303. Rise period X-rays 301, stable period X-rays 302, and fall period X-rays 303 have different X-ray energies. Thus, by obtaining X-ray images corresponding to radiation during periods separated by performing sampling and holding, a plurality of types of X-ray images of mutually different energies can be obtained.

The X-ray imaging apparatus 104 performs sampling using the noise sample-and-hold circuit 207N after exposure to the rise period X-rays 301, and further performs sampling using the signal sample-and-hold circuit 207S after exposure to the stable period X-rays 302. Subsequently, the X-ray imaging apparatus 104 reads the difference between the signal line 21N and the signal line 21S as an image. Here, a signal ($R_1$) of the rise period X-rays 301 is held in the noise sample-and-hold circuit 207N, and the sum ($R_1$+B) of the signal of the rise period X-rays 301 and a signal (B) of the stable period X-rays 302 is held in the signal sample-and-hold circuit 207S. Accordingly, an image 304 that corresponds to the signal of the stable period X-rays 302 is read.

Next, the X-ray imaging apparatus 104 performs sampling using the signal sample-and-hold circuit 207S again after the exposure to the fall period X-rays 303 and the reading of the image 304 are completed. Subsequently, the X-ray imaging apparatus 104 resets the photoelectric conversion element 201, performs sampling using the noise sample-and-hold circuit 207N again, and reads the difference between the signal line 21N and the signal line 21S as an image. Here, a signal of a state in which no X-ray exposure is performed is held in the noise sample-and-hold circuit 207N, and the sum ($R_1$+B+$R_2$) of the signal of the rise period X-rays 301, the signal of the stable period X-rays 302, and a signal ($R_2$) of the fall period X-rays 303 is held in the signal sample-and-hold circuit 207S. Accordingly, an image 306 that corresponds to the signal of the rise period X-rays 301, the signal of the stable period X-rays 302, and the signal of the fall period X-rays 303 is read. Subsequently, by calculating the difference between the image 306 and the image 304, an image 305 that corresponds to the sum of the rise period X-rays 301 and the fall period X-rays 303 is obtained. This calculation may be performed by the X-ray imaging apparatus 104 or by the imaging control apparatus 103.

The timings of the resetting of the photoelectric conversion element 201 and the sample-and-hold circuit section 207 are determined using a synchronization signal 307 that indicates that the exposure to X-rays from the X-ray generation apparatus 101 has started. A configuration of measuring the tube current of the X-ray generation apparatus 101 and determining whether or not the current value exceeds a preset threshold may be adopted as the method for detecting the start of X-ray exposure, but there is no limitation to this. For example, a configuration may be adopted in which the start of X-ray exposure is detected by, after the resetting of the photoelectric conversion element 201 is completed, repeating reading from the pixel 20 and determining whether or not the pixel value exceeds a preset threshold.

Alternatively, a configuration may be adopted in which an X-ray detector that is different from the two-dimensional detector 106 is built into the X-ray imaging apparatus 104, and the start of X-ray exposure is detected by determining whether or not a measurement value of the X-ray detector exceeds a preset threshold, for example. In any case, the sampling using the signal sample-and-hold circuit 207S, the sampling using the noise sample-and-hold circuit 207N, and the resetting of the photoelectric conversion element 201 are performed after a predetermined amount of time elapses from when the synchronization signal 307 indicating the start of X-ray exposure is input.

In such a manner, the image 304 corresponding to the stable period of a pulse X-ray beam and the image 305 corresponding to the sum of the rise period and the fall period of the pulse X-ray beam are obtained. These two X-ray images are formed through exposure to X-rays having mutually different energies, and thus energy subtraction processing can be performed by performing computation between these X-ray images.

Figure 4:
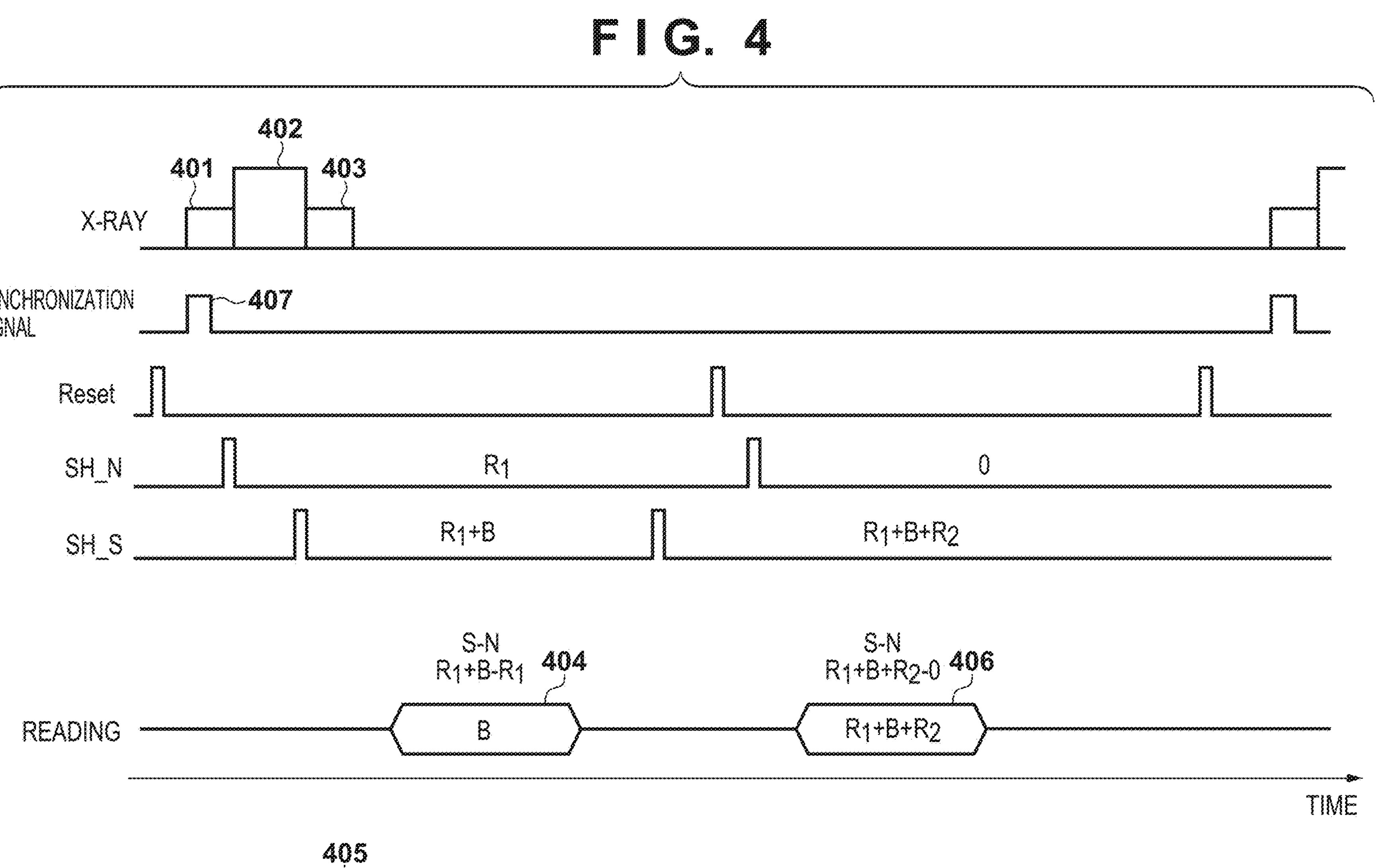
FIG. 4 is a timing chart of the X-ray imaging apparatus according to the embodiment.

FIG. 4 illustrates driving timings of the X-ray imaging apparatus 104 when energy subtraction is performed in the X-ray imaging system according to the embodiment. The drive timings illustrated in FIG. 4 differ from the drive timings illustrated in FIG. 3 in that the tube voltage of the X-ray generation apparatus 101 is actively switched.

First, the X-ray generation apparatus 101 performs exposure to low-energy X-rays 401 after the photoelectric conversion element 201 is reset. In this state, the X-ray imaging apparatus 104 performs sampling using the noise sample-and-hold circuit 207N. Subsequently, the X-ray generation apparatus 101 switches the tube voltage and performs exposure to high-energy X-rays 402. In this state, the X-ray imaging apparatus 104 performs sampling using the signal sample-and-hold circuit 207S. Subsequently, the X-ray generation apparatus 101 switches the tube voltage and performs exposure to low-energy X-rays 403. The X-ray imaging apparatus 104 reads the difference between the signal line 21N and the signal line 21S as an image. Here, a signal ($R_1$) of the low-energy X-rays 401 is held in the noise sample-and-hold circuit 207N, and the sum ($R_1$+B) of the signal of the low-energy X-rays 401 and a signal (B) of the high-energy X-rays 402 is held in the signal sample-and-hold circuit 207S. Accordingly, an image 404 that corresponds to the signal of the high-energy X-rays 402 is read.

Next, the X-ray imaging apparatus 104 performs sampling using the signal sample-and-hold circuit 207S again after the exposure to the low-energy X-rays 403 and the reading of the image 404 are completed. Subsequently, the X-ray imaging apparatus 104 resets the photoelectric conversion element 201, performs sampling using the noise sample-and-hold circuit 207N again, and reads the difference between the signal line 21N and the signal line 21S as an image. Here, a signal of a state in which no X-ray exposure is performed is held in the noise sample-and-hold circuit 207N, and the sum ($R_1$+B+$R_2$) of the signal of the low-energy X-rays 401, the signal of the high-energy X-rays 402, and a signal ($R_2$) of the low-energy X-rays 403 is held in the signal sample-and-hold circuit 207S. Accordingly, an image 406 that corresponds to the signal of the low-energy X-rays 401, the signal of the high-energy X-rays 402, and the signal of the low-energy X-rays 403 is read.

Subsequently, by calculating the difference between the image 406 and the image 404, an image 405 that corresponds to the sum of the low-energy X-rays 401 and the low-energy X-rays 403 is obtained. This calculation may be performed by the X-ray imaging apparatus 104 or by the imaging control apparatus 103. The synchronization signal 407 is similar to the synchronization signal in FIG. 3. By obtaining images while actively switching the tube voltage in such a manner, the energy difference between the low-energy and high-energy radiation images can be increased so as to be greater than that according to the method in FIG. 3.

Next, energy subtraction processing by the imaging control apparatus 103 will be described. The energy subtraction processing in the embodiment is divided into three stages, namely correction processing by the correction unit 132, signal processing by the signal processing unit 133, and image processing by the image processing unit 134. Each process will be described below.

The correction processing is processing in which a plurality of radiation images obtained from the X-ray imaging apparatus 104 are processed to generate a plurality of images to be used in the later-described signal processing in the energy subtraction processing.

Figure 5:
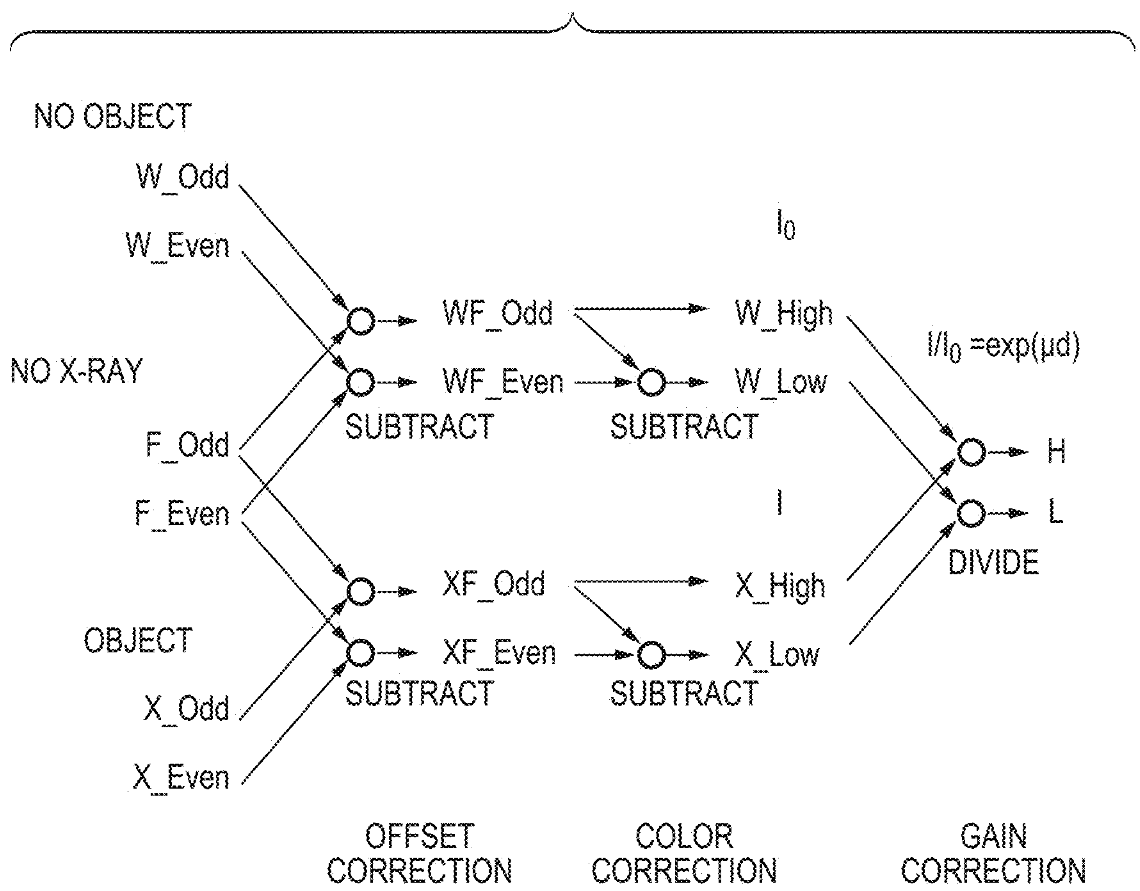
FIG. 5 is a diagram for describing correction processing according to the embodiment.

FIG. 5 illustrates a block diagram of the correction processing for the energy subtraction processing according to the embodiment. First, the obtaining unit 131 causes the X-ray imaging apparatus 104 to perform imaging in a state in which no X-ray exposure is performed, and obtains images according to the driving illustrated in FIG. 3 or FIG. 4. Two images are read as a result of the driving. In the following, the first image (image 304 or image 404) is referred to as F_ODD, and the second image (image 306 or image 406) is referred to as F_EVEN. F_ODD and F_EVEN are images corresponding to fixed pattern noise (FPN) of the X-ray imaging apparatus 104.

Next, the obtaining unit 131 exposes the X-ray imaging apparatus 104 to X-rays in a state in which no object is present and causes the X-ray imaging apparatus 104 to perform imaging to obtain gain correction images that are output from the X-ray imaging apparatus 104 according to the driving illustrated FIG. 3 or FIG. 4. As in the above-described case, two images are read as a result of this driving. In the following, the first gain-correction image (image 304 or image 404) is referred to as W_ODD, and the second gain-correction image (image 306 or image 406) is referred to as W_EVEN. W_ODD and W_EVEN are images corresponding to the sum of the FPN of the X-ray imaging apparatus 104 and an X-ray-based signal. The correction unit 132 obtains images WF_ODD and WF_EVEN from which the FPN of the X-ray imaging apparatus 104 has been removed by subtracting F_ODD from W_ODD and subtracting F_EVEN from W_EVEN. This is referred to as offset correction.

WF_ODD is an image that corresponds to the stable period X-rays 302, and WF_EVEN is an image that corresponds to the sum of the rise period X-rays 301, the stable period X-rays 302, and the fall period X-rays 303. Accordingly, the correction unit 132 obtains an image that corresponds to the sum of the rise period X-rays 301 and the fall period X-rays 303 by subtracting WF_ODD from WF_EVEN. Processing in which an image that corresponds to X-rays of specific periods separated by performing sampling and holding is obtained by performing subtraction using a plurality of images in such a manner is referred to as color correction. The energies of the rise period X-rays 301 and the fall period X-rays 303 are lower than the energy of the stable period X-rays 302. Accordingly, by performing the color correction and subtracting WF_ODD from WF_EVEN, a low-energy image W_Low without an object can be obtained. Furthermore, a high-energy image W_High without an object can be obtained from WF_ODD.

Next, the obtaining unit 131 exposes the X-ray imaging apparatus 104 to X-rays in a state in which an object is present and causes the X-ray imaging apparatus 104 to perform imaging to obtain images that are output from the X-ray imaging apparatus 104 according to the driving illustrated FIG. 3 or FIG. 4. Here, two images are read. In the following, the first image (image 304 or image 404) is referred to as X_ODD, and the second image (image 306 or image 406) is referred to as X_EVEN. By performing offset correction and color correction similar to those in the case in which no object is present, the correction unit 132 obtains a low-energy image X_Low with the object and a high-energy image X_High with the object.

Here, [Math. 1] below holds true, where d is the thickness of the object, μ is a linear attenuation coefficient of the object, $I_0$ is the output from a pixel 20 when the object is not present, and I is the output from the pixel 20 when the object is present.

$$I = I_0 \exp(\mu d) \quad \text{[Math. 1]}$$

[Math. 2] below can be obtained by transforming [Math. 1]. The right side of [Math. 2] indicates the transmittance of the object. The transmittance of the object is a real number between 0 and 1.

$$I/I_0 = \exp(\mu d) \quad \text{[Math. 2]}$$

Accordingly, the correction unit 132 obtains an image of transmittance L at low energy (hereinafter also referred to as "low-energy image L") by dividing the low-energy image X_Low with the object by the low-energy image W_Low without the object. Similarly, the correction unit 132 obtains an image of transmittance H at high energy (hereinafter also referred to as "high-energy image H") by dividing the high-energy image X_High with the object by the high-energy image W_High without the object. Processing in which images (L, H) of transmittance at low energy and transmittance at high energy are each obtained by dividing an image obtained based on radiation images obtained with the object by an image obtained based on radiation images obtained without the object in such a manner is referred to as gain correction.

Figure 6:
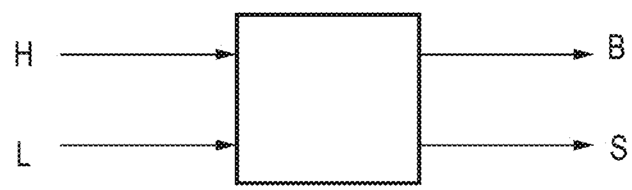
FIG. 6 is a block diagram of signal processing according to the embodiment.

FIG. 6 illustrates a block diagram of the signal processing in the energy subtraction processing according to the embodiment. The signal processing unit 133 generates material decomposition images using a plurality of images obtained from the correction unit 132. In the following, processing for generating material decomposition images including a bone thickness image B (hereinafter also referred to as a bone image B) and a soft tissue thickness image S (hereinafter also referred to as a soft tissue image S) will be described. The signal processing unit 133, by performing the following processing, obtains a bone thickness image B and a soft tissue thickness image S from the image of transmittance L at low energy and the image of transmittance H at high energy obtained as a result of the correction illustrated in FIG. 5.

First, [Math. 3] below holds true, where E is the X-ray photon energy, N(E) is the number of photons at the energy E, B is the thickness in the bone thickness image, S is the thickness in the soft tissue thickness image, $\mu_B(E)$ is a linear attenuation coefficient of bone at the energy E, $\mu_S(E)$ is a linear attenuation coefficient of soft tissue at the energy E, and $I/I_0$ is transmittance.

$$I/I_0 = \frac{\int_0^\infty N(E)\exp\{-\mu_B(E)B - \mu_S(E)S\}EdE}{\int_0^\infty N(E)EdE} \quad \text{[Math. 3]}$$

The number of photons N(E) at the energy E corresponds to an X-ray spectrum. The X-ray spectrum can be obtained through simulation or actual measurement. Furthermore, the linear attenuation coefficient $\mu_B(E)$ of bone at the energy E and the linear attenuation coefficient $\mu_S(E)$ of soft tissue at the energy E can be obtained from a database such as that provided by the National Institute of Standards and Technology (NIST). Accordingly, based on [Math. 3], the transmittance $I/I_0$ can be calculated for a thickness B in the bone thickness image, a thickness S in the soft tissue thickness image, and an X-ray spectrum N(E).

Here, in regard to the transmittance in the image L and the transmittance in the image H, the equations in [Math. 4] below hold true, where $N_L(E)$ is the low-energy X-ray spectrum, and $N_H(E)$ is the high-energy X-ray spectrum. Note that, in the following description, the transmittance in the image L indicated in [Math. 4] is also simply referred to as the low-energy transmittance L, and the transmittance in the image H indicated in [Math. 4] is also simply referred to as the high-energy transmittance H.

[Math. 4]

$$L = \frac{\int_0^\infty N_L(E)\exp\{-\mu_B(E)B - \mu_S(E)S\}EdE}{\int_0^\infty N_L(E)EdE}$$

$$H = \frac{\int_0^\infty N_H(E)\exp\{-\mu_B(E)B - \mu_S(E)S\}EdE}{\int_0^\infty N_H(E)EdE}$$

By solving the non-linear system of equations in [Math. 4], the thickness B in the bone thickness image and the thickness S in the soft tissue thickness image can be obtained. Here, as a representative method for solving the non-linear system of equations, a case will be described in which the Newton-Raphson method is used. First, the high-energy transmittance $H^m$ after an mth iteration and the low-energy transmittance $L^m$ after the mth iteration can be expressed using [Math. 5] below, where m is the number of iterations of the Newton-Raphson method, $B^m$ is the bone thickness after the mth iteration, and $S^m$ is the soft tissue thickness after the mth iteration.

[Math. 5]

$$L^m = \frac{\int_0^\infty N_L(E)\exp\{-\mu_B(E)B^m - \mu_S(E)S^m\}EdE}{\int_0^\infty N_L(E)EdE}$$

$$H^m = \frac{\int_0^\infty N_H(E)\exp\{-\mu_B(E)B^m - \mu_S(E)S^m\}EdE}{\int_0^\infty N_H(E)EdE}$$

Furthermore, the change rate of transmittance when there is a minute change in thickness is expressed using [Math. 6] below.

[Math. 6]

$$\frac{\partial H^m}{\partial B^m} = \frac{\int_0^\infty -\mu_B(E)N_H(E)\exp\{-\mu_B(E)B^m - \mu_S(E)S^m\}EdE}{\int_0^\infty N_H(E)EdE}$$

$$\frac{\partial L^m}{\partial B^m} = \frac{\int_0^\infty -\mu_B(E)N_L(E)\exp\{-\mu_B(E)B^m - \mu_S(E)S^m\}EdE}{\int_0^\infty N_L(E)EdE}$$

$$\frac{\partial H^m}{\partial S^m} = \frac{\int_0^\infty -\mu_S(E)N_H(E)\exp\{-\mu_B(E)B^m - \mu_S(E)S^m\}EdE}{\int_0^\infty N_H(E)EdE}$$

-continued $$\frac{\partial L^m}{\partial S^m} = \frac{\int_0^\infty -\mu_S(E)N_L(E)\exp\{-\mu_B(E)B^m - \mu_S(E)S^m\}EdE}{\int_0^\infty N_L(E)EdE}$$

Here, using the high-energy transmittance H and the low-energy transmittance L, the bone thickness $B^{m+1}$ and the soft-tissue thickness $S^{m+1}$ after the (m+1)th iteration are expressed using [Math. 7] below.

[Math. 7]

$$\begin{bmatrix} B^{m+1} \\ S^{m+1} \end{bmatrix} = \begin{bmatrix} B^m \\ S^m \end{bmatrix} + \begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} \begin{bmatrix} H - H^m \\ L - L^m \end{bmatrix}$$

According to the Cramer's rule, the inverse matrix of the 2×2 matrix can be expressed using [Math. 8] below, where det is the determinant.

[Math. 8]

$$\det = \frac{\partial H^m}{\partial B^m}\frac{\partial L^m}{\partial S^m} - \frac{\partial H^m}{\partial S^m}\frac{\partial L^m}{\partial B^m}$$

$$\begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} = \frac{1}{\det}\begin{bmatrix} \frac{\partial L^m}{\partial S^m} & -\frac{\partial H^m}{\partial S^m} \\ -\frac{\partial L^m}{\partial B^m} & \frac{\partial H^m}{\partial B^m} \end{bmatrix}$$

Accordingly, [Math. 9] below can be obtained by substituting [Math. 8] into [Math. 7].

[Math. 9]

$$B^{m+1} = B^m + \frac{1}{\det}\frac{\partial L^m}{\partial S^m}(H - H^m) - \frac{1}{\det}\frac{\partial H^m}{\partial S^m}(L - L^m)$$

$$S^{m+1} = S^m - \frac{1}{\det}\frac{\partial L^m}{\partial B^m}(H - H^m) + \frac{1}{\det}\frac{\partial H^m}{\partial B^m}(L - L^m)$$

By repeating such calculation, the difference between the high-energy transmittance $H^m$ after the mth iteration and the actually-measured high-energy transmittance H infinitely approaches 0. The same applies also to the low-energy transmittance L. Thus, the bone thickness $B^m$ after the mth iteration converges to the bone thickness B, and the soft tissue thickness $S^m$ after the mth iteration converges to the soft tissue thickness S. The non-linear system of equations shown in [Math. 4] can be solved in such a manner. Accordingly, by calculating [Math. 4] for all pixels, a bone thickness image B and a soft tissue thickness image S can be obtained from the image of transmittance L at low energy and the image of transmittance H at high energy.

Note that, while a bone thickness image B and a soft tissue thickness image S are calculated in the embodiment, the technique disclosed herein is not limited to such an embodiment. For example, the thickness W of water and the thickness I of a contrast agent may be calculated, the thicknesses of an acrylic resin (PMMA) and aluminum (AL) may be calculated as components of a phantom, or the thickness of a first material and a thickness of a second material that is different from the first material may be calculated. That is, decomposition may be performed into the thicknesses of any two kinds of materials.

Furthermore, the non-linear system of equations is solved using the Newton-Raphson method in the embodiment.

However, the technique disclosed herein is not limited to such an embodiment. For example, iterative solution methods such as the least-squares method and the bisection method may be used.

Furthermore, while the non-linear system of equations is solved using an iterative solution method in the embodiment, the technique disclosed herein is not limited to such an embodiment. Numerical integration needs to be performed in this process. Moreover, recalculation is necessary every time iterative calculation is performed m times. Furthermore, such computation would need to be performed for all pixels. Accordingly, there is a problem that the energy subtraction signal processing illustrated in FIG. 6 is very time-consuming. Especially since the present embodiment is based on the assumption that moving images will be captured, the permitted signal processing time is 1 frame or less. For example, if the frame rate is 20 fps, processing would not be completed in time unless the signal processing and the image processing are performed in 50 ms or less. Thus, a configuration may be adopted such that tables are generated preemptively by obtaining the bone thickness B and soft tissue thickness S corresponding to various combinations of the high-energy transmittance H and the low-energy transmittance L in advance, and the bone thickness B and soft tissue thickness S are obtained at high speed by referencing these tables.

Figure 7:
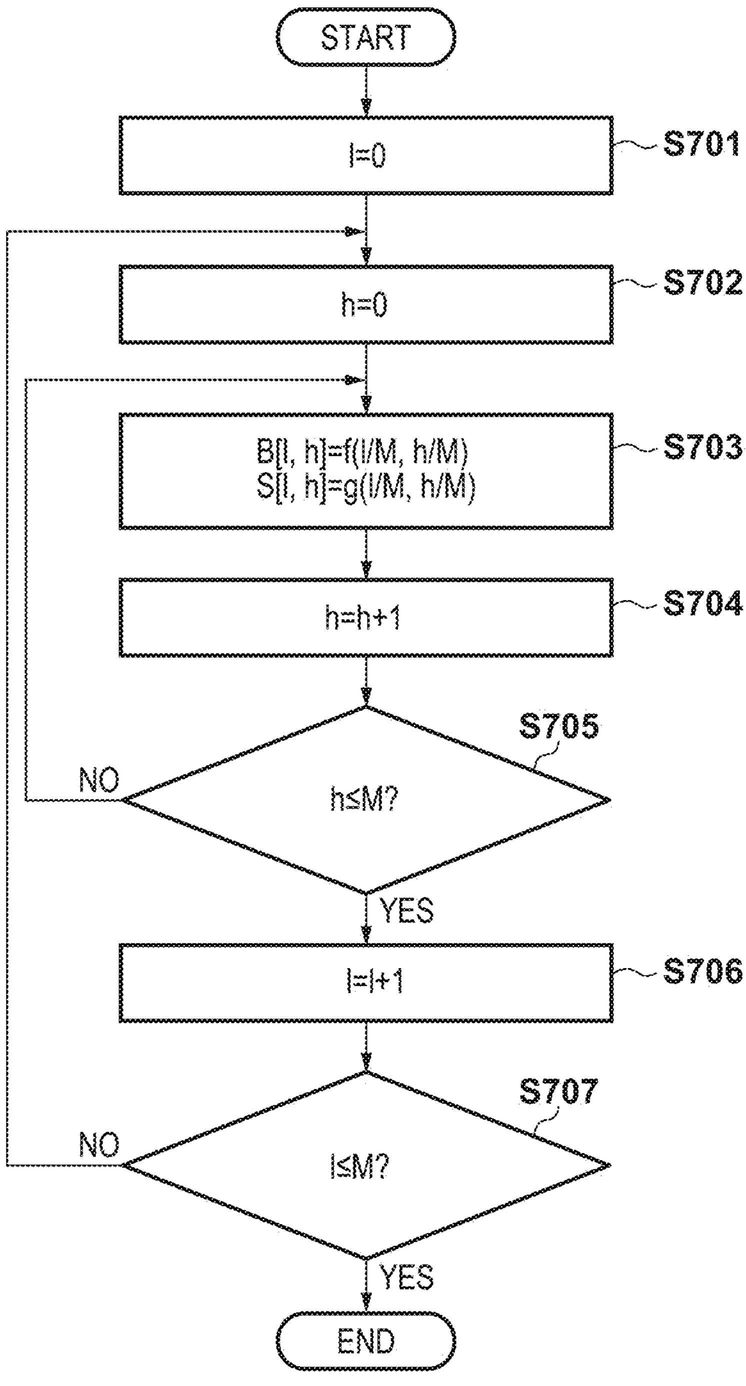
FIG. 7 is a flowchart for describing a flow of table generation according to the embodiment.

FIG. 7 is a flowchart describing a flow of table generation according to the present embodiment. Let M be a division count of the tables, and l and h be a low-energy coordinate and a high-energy coordinate in the tables, respectively. Note that the table coordinates l and h are integers. First, the imaging control apparatus 103 initializes the low-energy coordinate to l=0 (step S701), and then initializes the high-energy coordinate to h=0 (step S702).

Next, the imaging control apparatus 103 obtains the low-energy transmittance L[l] at the coordinate l and the high-energy transmittance H[h] at the coordinate h using [Math. 10] below.

$$H[h] = h/M \qquad L[l] = l/M \tag{Math. 10}$$

For the low-energy transmittance L[l] and the high-energy transmittance H[h] obtained in such a manner, the non-linear system of equations shown in [Math. 4] is solved to obtain the bone thickness B and the soft tissue thickness S. The results are stored in a table B[l, h] corresponding to the bone thickness B and a table S[l, h] corresponding to the soft tissue thickness S (step S703). Subsequently, the imaging control apparatus 103 sets h+l to h (step S704). If the high-energy coordinate h has not exceeded the table division count M (NO in step S705), the imaging control apparatus 103 repeats the processing starting from step S703. If the high-energy coordinate h has exceeded the table division count M (YES in step S705), the imaging control apparatus 103 sets l+1 to l (step S706). Then, if the low-energy coordinate l has not exceeded the table division count M (NO in step S707), the imaging control apparatus 103 sets 0 to h (step S702) and repeats the processing in steps S703 to S705. If the low-energy coordinate l has exceeded the table division count M (YES in step S707), the generation of tables is terminated. In such a manner, the bone thickness B and the soft-tissue thicknesses S can be obtained for all combinations of l and h and stored in tables.

Figure 8:
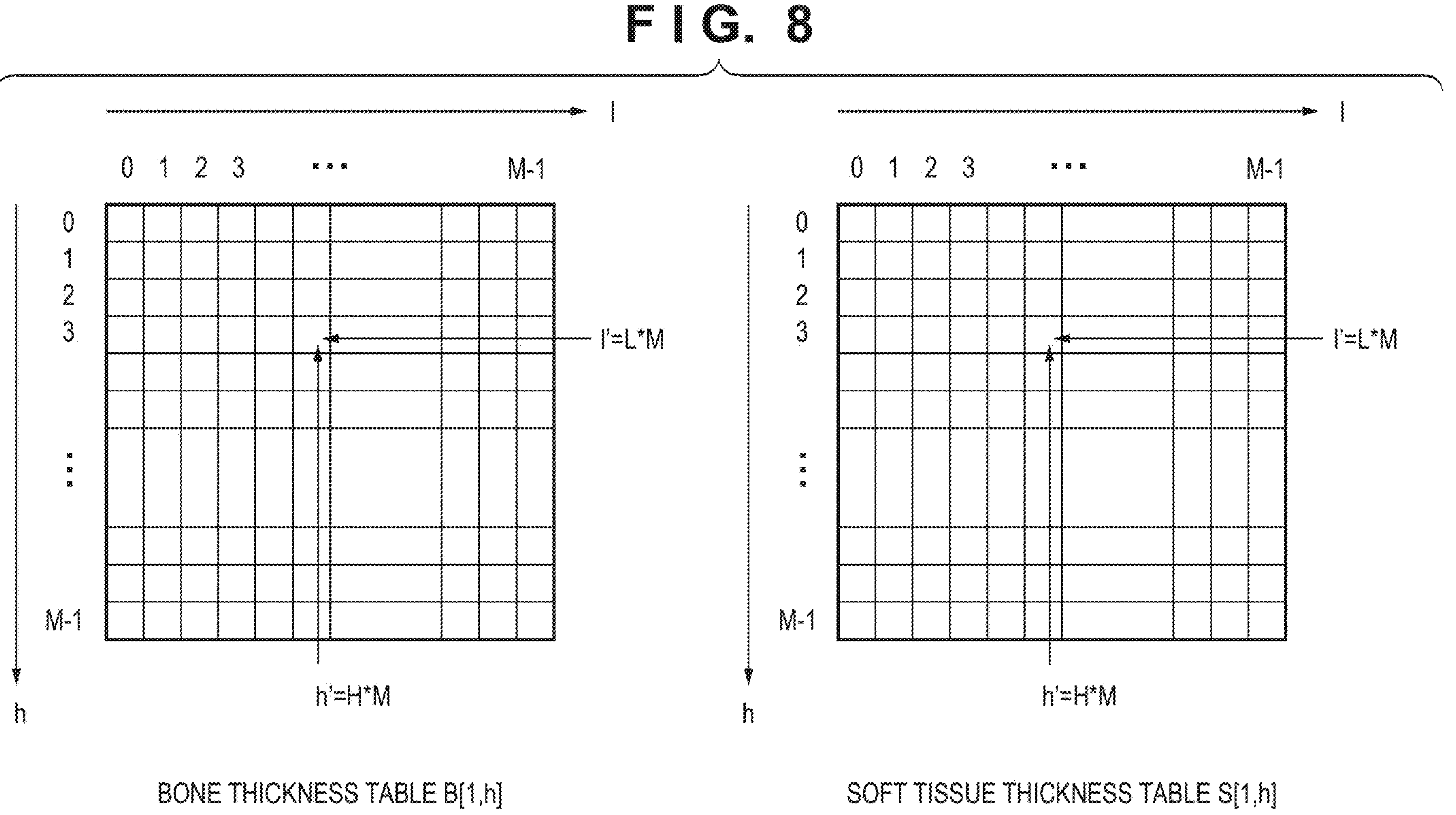
FIG. 8 is a schematic diagram of tables according to the embodiment.

FIG. 8 is a schematic diagram of the tables according to the present embodiment. These tables are two-dimensional tables in which a bone thickness and a soft tissue thickness are registered for each combination of transmittance indicated by a high-energy image and transmittance indicated by a low-energy image. Let L and H be the low-energy transmittance and high-energy transmittance actually measured by a given pixel, respectively. Here, transmittance is converted into table coordinates l' and h' using [Math. 11] below.

$$h' = H * M \qquad l' = L * M \tag{Math. 11}$$

By using these coordinates and referencing the table B[l, h] corresponding to the bone thickness B, the bone thickness B can be obtained. The same applies also to soft tissue thickness. Here, the table coordinates l' and h' obtained are decimals. However, because the tables are stored in the form of arrays, the tables can be referenced using only integers. Accordingly, a configuration is adopted in which the coordinates l' and h' are converted into integers, and the bone thickness B and the soft tissue thickness S are then obtained by interpolation. For example, in order to obtain the bone thickness B and the soft tissue thickness S by bilinear interpolation, [Math. 12] below can be used, where l is a value obtained by converting the coordinate l' into an integer by rounding down the decimal places, and h is a value obtained by converting the coordinate h' into an integer by rounding down the decimal places.

$$\begin{aligned} B &= \{B[l, h](h+1-h') + B[l, h+1](h'-h)\}(l+1-l') + \\ &\quad \{B[l+1, h](h+1-h') + B[l+1, h+1](h'-h)\}(l'-l) \\ S &= \{S[l, h](h+1-h') + S[l, h+1](h'-h)\}(l+1-l') + \\ &\quad \{S[l+1, h](h+1-h') + S[l+1, h+1](h'-h)\}(l'-l) \end{aligned} \tag{Math. 12}$$

Accordingly, by generating the tables in advance, the bone thickness B and the soft tissue thickness S can be obtained with a calculation amount that is significantly less compared to that in a case in which the non-linear system of equations is solved. Such tables are valid unless the radiation spectrum N(E) changes. Because the radiation spectrum N(E) generally does not change while a moving image is being captured, it is sufficient that the tables be generated once before imaging. As a matter of course, the generation and referencing of the tables illustrated in FIGS. 7 and 8 are also similarly applicable when the thicknesses of any two materials are calculated. In such a manner, the energy subtraction signal processing illustrated in FIG. 6 can be performed with high accuracy and at a high speed.

In the present embodiment, the low-energy transmittance L[l] at a coordinate l and the high-energy transmittance H[h] at a coordinate h are obtained using [Math. 10]. In tables generated in such a manner, while the vertical-axis coordinates and the horizontal-axis coordinates respectively indicate high-energy transmittance H and low-energy transmittance L, transmittance from 0 to 1 would be divided at equal intervals in the tables. However, transmittance corresponding to the human-body composition and thickness often has a value near 0. Thus, a small table division count M may result in the occurrence of a case in which there is a large error between a value obtained by referencing a table and performing interpolation, and a value obtained by solving the non-linear system of equations. In view of this, a configuration can be adopted in which transmittance is obtained using [Math. 13] below, where k (0<k) is a constant determining a coordinate range.

$$H[h] = \exp(-k*h/M)$$ [Math. 13]

$$L[l] = \exp(-k*l/M)$$

In a case in which transmittance is obtained from coordinates using [Math. 13], the coordinates can be obtained using [Math. 14] below.

$$h' = -\ln(H[h])*M/k$$ [Math. 14]

$$l' = -\ln(L[l])*M/k$$

[Math. 14] can be used to reference the tables and perform interpolation. In the tables generated in such a manner, the vertical-axis coordinates and the horizontal-axis coordinates are −ln(H) and −ln(L), respectively. Accordingly, even if the transmittance value is near 0, the error between the value obtained by referencing a table and performing interpolation, and the value obtained by solving the non-linear system of equations can be reduced.

In the generation and referencing of tables in the present embodiment, there may be a combination of the high-energy transmittance H and the low-energy transmittance L for which there is no solution. For example, the high-energy transmittance H is usually higher than the low-energy transmittance L. Accordingly, in the tables generated using [Math. 10] or [Math. 13], solutions cannot be obtained for regions in which H<L holds true.

In the present embodiment, coordinates may be selected so that regions on the tables for which solutions cannot be obtained decrease. For example, ln(L)/ln(H) and −ln(H), etc., may be used as the vertical-axis coordinate and the horizontal-axis coordinate, respectively. Furthermore, when the tables are referenced in the present embodiment, coordinates lying outside the ranges of the tables may be designated, and regions for which solutions cannot be obtained may be referenced. In such cases, a configuration is adopted in which a value of a region which is near the designated coordinates and for which there is a solution is used.

In the signal processing in FIG. 6, the high-energy transmittance H and the low-energy transmittance L are obtained using [Math. 4]; here, transmittance obtained using [Math. 4] is a theoretical value estimated from the linear attenuation coefficients and the spectrum.

However, in actual imaging, transmittance may increase due to scattered rays generated inside the object. Accordingly, errors may occur in the bone thickness B and the soft-tissue thickness S if the signal processing in FIG. 6 is performed using high-energy transmittance H' including scattered rays and low-energy transmittance L' including scattered rays, in which the generation of scattered rays is taken into consideration. In order to solve this problem, in the present embodiment, scattered rays are connected in order to reduce the effect of scattered rays in the signal processing.

Figures 9, 10:
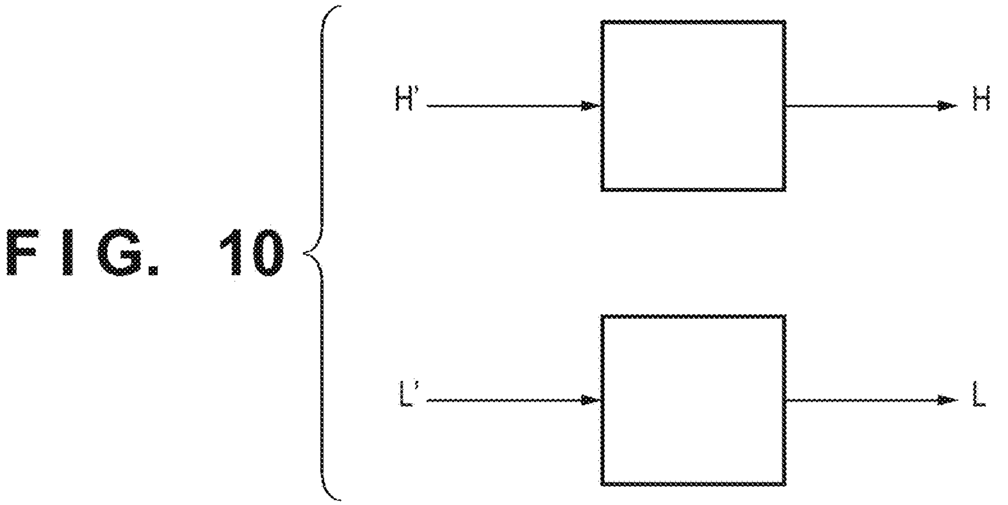
FIG. 9 is a diagram illustrating an example of tables for scattered ray correction according to the embodiment.
FIG. 10 is a block diagram of scattered ray correction processing according to the embodiment.

In order to correct scattered rays, the scattered ray dose needs to be estimated, and, in the present embodiment, tables for scattered ray correction are used to estimate the scattered ray dose. FIG. 9 is a diagram illustrating an example of tables for scattered ray correction according to the embodiment.

The tables for scattered ray correction shown in FIG. 9 are created by placing a flat plate, for example, between the two-dimensional detector 106 and the X-ray generation apparatus 101 (X-ray source), and measuring the transmittance when the flat plate is irradiated with X-rays. When the X-ray irradiation range is sufficiently enlarged, scattered rays are generated inside the flat plate. The high-energy transmittance measured in this state is referred to as transmittance $H_{real}$ including scattered rays.

Furthermore, when the X-ray irradiation range is reduced, scattered rays generated inside the flat plate decrease, and the transmittance measured in this state approaches the theoretical value of transmittance obtained using [Math. 4]. The high-energy transmittance measured in the state in which the X-ray irradiation range has been reduced is referred to as transmittance $H_{ideal}$ not including scattered rays.

By preparing a plurality of flat plates (n patterns, where n is an integer of 2 or more) of the same material that have different thicknesses and repeating a similar measurement while changing the flat-plate thickness S[n], high-energy transmittance $H_{real}$[n] including scattered rays and high-energy transmittance $H_{ideal}$[n] not including scattered rays are measured and stored to a table 901 for scattered ray correction. Thus, in regard to high-energy transmittance, transmittance $H_{real}$[n] including scattered rays and transmittance $H_{ideal}$[n] not including scattered rays are stored for each flat-plate thickness S[n] in the table 901 for scattered ray correction.

Furthermore, a similar measurement is performed in regard to low-energy transmittance. That is, measurement in a state in which the X-ray irradiation range is sufficiently enlarged and measurement in a state in which the X-ray irradiation range is reduced are performed, and, in regard to low-energy transmittance, transmittance $L_{real}$[n] including scattered rays and transmittance $L_{ideal}$[n] not including scattered rays are obtained and stored in a table 902 for scattered ray correction. Thus, in regard to low-energy transmittance, transmittance $L_{real}$[n] including scattered rays and transmittance $L_{ideal}$[n] not including scattered rays are stored for each flat-plate thickness S[n] in the table 902 for scattered ray correction.

Note that, as the material of the flat plate, an acrylic resin (PMMA) having a linear attenuation coefficient close to that of soft tissue (for example, fat) can be used, for example. Similarly, Tough Water, which has a linear attenuation coefficient similar to that of water, or water itself may be accommodated in a container and used. Alternatively, aluminum (AL) having a linear attenuation coefficient close to that of bone, which is a hard material, may be used, for example.

Furthermore, the object to be imaged is not limited to having the shape of a flat plate, and the tables 901 and 902 for scattered ray correction may be created by imaging a circular cylinder, an elliptic cylinder, or the like, for example. Furthermore, while an example in which transmittance including scattered rays and transmittance not including scattered rays are obtained by experimentation has been described in the description of FIG. 9, there is no limitation to this example; transmittance including scattered rays and transmittance not including scattered rays may be obtained from a database or may be obtained by simulation.

The signal processing unit 133 obtains transmittance not including scattered rays that corresponds to a thickness of a predetermined material by performing correction in which transmittance including scattered rays and transmittance not including scattered rays that are stored in the storage unit 136 are used. FIG. 10 is a block diagram of scattered ray correction processing according to the embodiment. In the scattered ray correction processing, the signal processing unit 133 obtains transmittance H not including scattered rays at high energy from transmittance H' including scattered rays at high energy using the table 901 for scattered ray correction shown in FIG. 9.

The signal processing unit 133 performs a search in the table 901 for scattered ray correction for high energy to obtain information (n) regarding a thickness of the material for which the high-energy transmittance H' including scattered rays is no less than the transmittance $H_{real}[n]$ including scattered rays and less than the transmittance $H_{real}[n+1]$ including scattered rays ($H_{real}[n] \leq H' < H_{real}[n+1]$).

By using the information (n) regarding the thickness of the material, the signal processing unit 133 obtains transmittance H not including scattered rays from high-energy transmittance H' including scattered rays by performing correction (interpolation) of data in the table 901 using [Math. 15A] below.

$$H = H_{ideal}[n]*(H_{real}[n+1]-H')/(H_{real}[n+1]-H_{real}[n]) + H_{ideal}[n+1]*(H'-H_{real}[n])/(H_{real}[n+1]-H_{real}[n]) \quad \text{[Math. 15A]}$$

This similarly applies also to low-energy transmittance L' including scattered rays and low-energy transmittance L not including scattered rays. In such a manner, scattered rays can be corrected by converting high-energy transmittance H' including scattered rays and low-energy transmittance L' including scattered rays into high-energy transmittance H not including scattered rays and low-energy transmittance L not including scattered rays, respectively.

In the tables for scattered ray correction described with reference to FIG. 9, the relationship between transmittance ($H_{real}$ and $L_{real}$) including scattered rays and transmittance ($H_{ideal}$ and $L_{ideal}$) not including scattered rays was stored for each thickness S[n].

However, the tables for scattered ray correction are not limited to the examples in FIG. 9, and, for example, a configuration may be adopted in which values obtained by expressing X-ray components in the form of a ratio are stored in tables, with a region in which X-rays from the X-ray generation apparatus 101 directly reach the two-dimensional detector 106 being regarded a primary-radiation region. For example, a Scatter Primary Ratio (SPR) as indicated in [Math. 15B], which is the ratio between a scattered-ray component (Scatter) and a primary-radiation component (Primary), may be stored. In the description of mathematical formulae hereinafter, the scattered-ray component (Scatter) is also simply referred to as "scattered-ray component S" or "S", and the primary-radiation component (Primary) is also simply referred to as "primary-radiation component P" or "P".

$$SPR = \text{scattered-ray component } S/\text{primary-radiation component } P \quad \text{[Math. 15B]}$$

Here, transmittance $H_{real}$ including scattered rays at high energy corresponds to the total of the primary-radiation component P and the scattered-ray component S (primary-radiation component P+scattered-ray component S), and transmittance $H_{ideal}$ not including scattered rays at high energy corresponds to the primary-radiation component P ($H_{ideal}$=primary-radiation component P).

From the relationship between the scattered-ray component S and the primary-radiation component P, the relationship between transmittance $H_{real}$ including scattered rays and transmittance $H_{ideal}$ not including scattered rays can be indicated using [Math. 15C]. Furthermore, the relationship between SPR, and transmittance $H_{real}$ including scattered rays and transmittance $H_{ideal}$ not including scattered rays can be indicated using [Math. 15D] below.

$$\text{Scattered-ray component } S = P + S - P = H_{real} - H_{ideal} \quad \text{[Math. 15C]}$$

$$SPR = S/P = (H_{real} - H_{ideal})/H_{ideal} \quad \text{[Math. 15D]}$$

By transforming [Math. 15D], transmittance $H_{ideal}$ not including scattered rays can be indicated as in [Math. 15E] below using transmittance $H_{real}$ including scattered rays and SPR.

$$\begin{aligned} SPR*H_{ideal} &= H_{real} - H_{ideal} \\ SPR*H_{ideal} + H_{ideal} &= H_{real} \\ (1+SPR)*H_{ideal} &= H_{real} \\ H_{ideal} &= H_{real}/(1+SPR) \end{aligned} \quad \text{[Math. 15E]}$$

Transmittance $H_{real}[n]$ including scattered rays and transmittance $H_{ideal}[n]$ not including scattered rays at thickness [n] can be indicated using [Math. 15F] below.

$$\begin{aligned} H_{ideal}[n] &= H_{real}[n]/(1+SPR[n]) \\ H_{ideal}[n+1] &= H_{real}[n+1]/(1+SPR[n+1]) \end{aligned} \quad \text{[Math. 15F]}$$

By substituting [Math. 15F] into [Math. 15A], [Math. 15G] for correcting transmittance using SPR, which is the ratio between the scattered-ray component and the primary-radiation component, can be obtained.

$$H = H_{real}[n]/(1+SPR[n])*(H_{real}[n+1]-H')/(H_{real}[n+1]-H_{real}[n]) + H_{real}[n+1]/(1+SPR[n+1])*(H'-H_{real}[n])/(H_{real}[n+1]-H_{real}[n]) \quad \text{[Math. 15G]}$$

In the processing in [Math. 15B] to [Math. 15G], a ratio between the scattered-ray component included in radiation and the primary-radiation component corresponding to radiation directly reaching the two-dimensional detector 106 from the X-ray generation apparatus 101 (radiation source) is stored in the storage unit 136 for each of multiple thicknesses of the predetermined material. The signal processing unit 133 obtains transmittance H not including scattered rays corresponding to a thickness of the predetermined material by performing correction in which the ratio SPR and transmittance $H_{real}$ including scattered rays are used.

Furthermore, the tables for scattered ray correction are not limited to the examples in FIG. 9, and, for example, a difference SB between transmittance $H_{real}$ including scattered rays and transmittance $H_{ideal}$ not including scattered rays may be stored. By using the difference SB, transmittance $H_{real}[n]$ including scattered rays and transmittance $H_{ideal}[n]$ not including scattered rays at thickness [n] can be indicated using [Math. 15H] below.

$$\text{Difference } SB = H_{real} - H_{ideal} \quad \text{[Math. 15H]}$$
$$H_{ideal}[n] = H_{real}[n] - SB[n]$$
$$H_{ideal}[n+1] = H_{real}[n+1] - SB[n+1]$$

By substituting [Math. 15H] into [Math. 15A], [Math. 15J] below for correcting transmittance using the difference SB between transmittance $H_{real}$ including scattered rays and transmittance $H_{ideal}$ not including scattered rays can be obtained.

$$H = (H_{real}[n] - SB[n]) * (H_{real}[n+1] - H')/(H_{real}[n+1] - H_{real}[n]) + (H_{real}[n+1] - SB[n+1]) * (H' - H_{real}[n])/(H_{real}[n+1] - H_{real}[n]) \quad \text{[Math. 15J]}$$

In the processing in [Math. 15H] to [Math. 15J], the difference SB between transmittance $H_{real}$ including scattered rays and transmittance $H_{ideal}$ not including scattered rays is stored in the storage unit 136 for each of multiple thicknesses of the predetermined material. The signal processing unit 133 obtains transmittance H not including scattered rays corresponding to a thickness of the predetermined material by performing correction in which the difference SB and transmittance $H_{real}$ including scattered rays are used.

Furthermore, in the description with reference to FIG. 10, scattered rays were corrected using tables for scattered ray correction. However, scattered ray correction is not limited to such an embodiment. For example, the relationship between transmittance including scattered rays and transmittance not including scattered rays may be approximated using a function, etc. For example, a configuration may be adopted such that a function associating transmittance $H_{ideal}$ not including scattered rays and transmittance $H_{real}$ including scattered rays with one another is obtained, and, when transmittance $H_{real}$ including scattered rays is inputted to this function as input, transmittance $H_{ideal}$ not including scattered rays can be obtained as an output of the function. In a case in which approximation with such a function is performed, the interpolation processing using [Math. 15A] to [Math. 15J] becomes unnecessary because the relationship between a pixel value including scattered rays and a pixel value not including scattered rays would be included in the function.

The tables for scattered ray correction shown in FIG. 9 are created by preparing n patterns (where n is an integer of 2 or more) of flat plates of the same material that have different thicknesses, and obtaining transmittance while changing the flat plate thickness S[n].

However, the actual object is formed from a plurality of materials, such as bone and soft tissue. If the types of materials forming the object change, the dose of scattered rays generated may also change. The present inventors performed scattered ray correction using the tables for scattered ray correction shown in FIG. 9, and discovered that non-negligible errors may occur in the transmittance H and transmittance L after correction in a case in which the object is formed from a plurality of materials.

Furthermore, it was discovered that non-negligible errors may also occur in the transmittance H and transmittance L after scattered ray correction also in a case in which the object is different from the material used to create the tables for scattered ray correction. The present inventors discovered the problem that, due to this, errors may occur in the bone thickness B and the soft-tissue thickness S obtained according to the signal processing shown in FIG. 6. In view of this, in the present embodiment, the present inventors propose scattered ray correction taking into consideration a plurality of materials (two materials), such as bone and soft tissue for example, forming the object.

In the present embodiment, information regarding transmittance including scattered rays obtained for each combination of a thickness of a first material and a thickness of a second material is stored in the storage unit 136. By correcting information obtained from the storage unit 136 based on a combination of a thickness of the first material and a thickness of the second material, the signal processing unit 133 obtains information regarding transmittance (H', L') including scattered rays for the combination.

FIG. 11 is a diagram illustrating tables for scattered ray correction in which two materials are taken into consideration according to the embodiment. The table 1101 shown in FIG. 11 is a table for correcting transmittance $H_{real}[m,n]$ including scattered rays at high energy, and the table 1102 shown in FIG. 11 is a table for correcting transmittance $L_{real}[m,n]$ including scattered rays at low energy. The tables 1101 and 1102 for scattered ray correction shown in FIG. 11, in which two materials are taken into consideration, can be created using the same method as that for the tables 901 and 902 for scattered ray correction shown in FIG. 9. Note that, while a table for correcting transmittance $H_{ideal}[m,n]$ not including scattered rays at high energy and a table for correcting transmittance $L_{ideal}[m,n]$ not including scattered rays at low energy can also be created in a similar manner as the tables 1101 and 1102, correction processing based on a combination of thicknesses of two materials can become complex and result in high computation load. Because transmittance $H_{ideal}$ not including scattered rays at high energy and transmittance $L_{ideal}$ not including scattered rays at low energy are substantially the same as transmittance H and transmittance L obtained by the theoretical calculation using [Math. 4], it is sufficient that information (H, L) obtained by the calculation in [Math. 4] be used for transmittance not including scattered rays.

In the creation of the tables 1101 and 1102, m patterns (where m is an integer of 2 or more) of flat plates of the first material that have different thicknesses and n patterns (where n is an integer of 2 or more) of flat plates of the second material, which is different from the first material, that have different thicknesses are prepared as flat plates to be placed between the two-dimensional detector 106 and the X-ray generation apparatus 101 (X-ray source). Measurement is performed in a state in which a flat plate of the first material and a flat plate of the second material are arranged so as to be placed one over the other in the direction in which X-rays are emitted from the X-ray generation apparatus 101 toward the two-dimensional detector 106.

Furthermore, a similar measurement is repeated while changing the combination of the thickness B[m] of the m patterns of flat plates of the first material and the thickness S[n] of the n patterns of flat plates of the second material. By performing such measurement, transmittance $H_{real}$[m,n] including scattered rays at high energy and transmittance $H_{ideal}$[m,n] not including scattered rays at high energy are measured (obtained). Furthermore, in regard to low energy, transmittance $L_{real}$[m,n] including scattered rays at low energy and transmittance $L_{ideal}$[m,n] not including scattered rays at low energy are similarly measured (obtained). By repeating measurement in which the combination of the thickness B[m] of the m patterns of flat plates of the first material and the thickness S[n] of the n patterns of flat plates of the second material is changed, the tables 1101 and 1102 for scattered ray correction shown in FIG. 11, in which two materials are taken into consideration, can be obtained.

In the scattered ray correction in which two materials (first material and second material) are taken into consideration, the signal processing unit 133 obtains bone thickness B and soft tissue thickness S not including scattered rays from transmittance H' including scattered rays at high energy and transmittance L' including scattered rays at low energy using the tables for scattered ray correction shown in FIG. 11, in which two materials are taken into consideration.

The signal processing unit 133 executes such processing in two stages, i.e., first processing and second processing.

(1) First processing: In regard to first radiation energy (high energy) in a case in which scattered rays are not included, the signal processing unit 133 generates a first function (function H'=h(B,S)) that, from a combination of a thickness of the first material (bone thickness B) and a thickness of the second material (soft tissue thickness S), outputs information regarding transmittance including scattered rays for the combination. Furthermore, in regard to second radiation energy (low energy) in a case in which scattered rays are not included, the signal processing unit 133 generates a second function (function L'=l(B,S)) that, from a combination of a thickness of the first material (bone thickness B) and a thickness of the second material (soft tissue thickness S), outputs information regarding transmittance including scattered rays for the combination. Specifically, the signal processing unit 133 generates, from bone thickness B and soft tissue thickness S not including scattered rays, the function H'=h(B,S) for obtaining transmittance H' including scattered rays at high energy and the function L'=l(B,S) for obtaining transmittance L' including scattered rays at low energy.

[Math. 4] described earlier is for obtaining transmittance H and transmittance L not including scattered rays from bone thickness B and soft tissue thickness S not including scattered rays. In the first processing, based on the data in tables 1101 and 1102, the signal processing unit 133 generates the function H'=h(B,S) for obtaining transmittance H' including scattered rays and the function L'=l(B,S) for obtaining transmittance L' including scattered rays as functions corresponding to [Math. 4] from bone thickness B and soft tissue thickness S not including scattered rays.

In the generation of the function H'=h(B,S), the signal processing unit 133 references table 1101. For example, if bone thickness B is 1.5, a search is performed in table 1101 for data corresponding to B=1 and B=2, and, if soft tissue thickness S is 13, a search is performed in table 1101 for data corresponding to S=10 and S=15. The signal processing unit 133 obtains, as the function H'=h(B,S), transmittance H' including scattered rays obtained by performing correction (interpolation) based on data found from table 1101 based on the combination of bone thickness B and soft-tissue thickness S.

In the generation of the function L'=l(B,S), the signal processing unit 133 references table 1102. For example, if bone thickness B is 1.5, a search is performed in table 1102 for data corresponding to B=1 and B=2, and, if soft tissue thickness S is 13, a search is performed in table 1102 for data corresponding to S=10 and S=15. The signal processing unit 133 obtains, as the function L'=l(B,S), transmittance L' including scattered rays obtained by performing correction (interpolation) based on data found from table 1102 based on the combination of bone thickness B and soft tissue thickness S.

(2) Second processing: Next, the signal processing unit 133 uses the functions H'=h(B,S) and L'=l(B,S) obtained in the first processing to obtain bone thickness B and soft tissue thickness S not including scattered rays from transmittance H' including scattered rays at high energy and transmittance L' including scattered rays at low energy.

Figure 12:
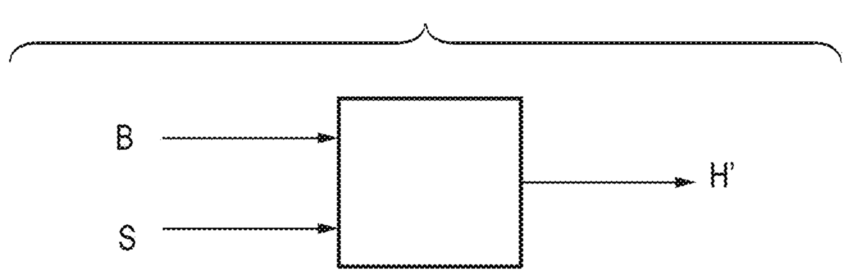
FIG. 12 is a block diagram of transmittance calculation in which two materials are taken into consideration according to the embodiment.
Figure 12:
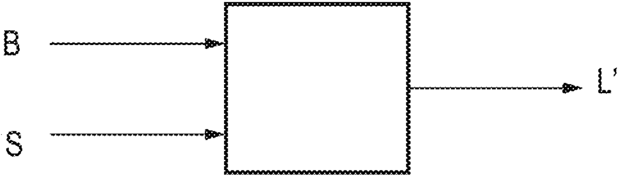

FIG. 12 is a block diagram of transmittance calculation relating to the first processing in the embodiment, in which two materials are taken into consideration. In processing in the case in which scattered rays are not included, the computation processing in [Math. 4] is included in the block diagram in FIG. 6; meanwhile, in the case in which scattered rays are included, correction (interpolation) processing obtained from the data in tables 1101 and 1102 is included in place of the computation processing in [Math. 4].

The signal processing unit 133 obtains, from bone thickness B and soft tissue thickness S not including scattered rays set as initial values, the function H'=h(B,S) for obtaining transmittance H' including scattered rays at high energy and the function L'=l(B,S) for obtaining transmittance L' including scattered rays at low energy. The signal processing unit 133 obtains the functions H'=h(B,S) and L'=l(B,S) by performing a search and interpolation using tables 1101 and 1102.

First, the signal processing unit 133 performs a search in table 1101 regarding the two materials using thickness B to obtain m for which B[m]≤B<B[m+1] holds true.

Similarly, the signal processing unit 133 performs a search in the table 1101 regarding the two materials using thickness S to obtain n for which S[n]≤S<S[n+1] holds true.

Furthermore, the signal processing unit 133 obtains transmittance H' including scattered rays as the function H'=h(B, S) by using [Math. 16A] below and performing correction (interpolation) on the data obtained as a result of the search in table 1101. As a result of the correction, the signal processing unit 133 obtains information H' regarding transmittance including scattered rays at the first radiation energy (high energy).

[Math. 16A]

$$H'[n] = H_{ideal}[m,n]*(B[m+1]-B)/(B[m+1]-B[m]) + H_{ideal}[m+1,n]*(B-B[m])/(B[m+1]-B[m])$$

$$H'[n+1] = H_{ideal}[m,n+1]*(B[m+1]-B)/(B[m+1]-B[m]) + H_{ideal}[m+1,n+1]*(B-B[m])/(B[m+1]-B[m])$$

-continued $$H' = H'[n] * (S[n+1] - S)/(S[n+1] - S[n]) + H'[n+1] * (S - S[n])/(S[n+1] - S[n])$$

In regard to low-energy transmittance L', the signal processing unit 133 similarly obtains transmittance L' including scattered rays as the function L'=I(B,S) by using [Math. 16B] below and performing correction (interpolation) on the data obtained as a result of the search in table 1102. As a result of the correction, the signal processing unit 133 obtains information L' regarding transmittance including scattered rays at the second radiation energy (low energy).

$$L'[n] = L_{ideal}[m, n] * (B[m+1] - B)/(B[m+1] - B[m]) + L_{ideal}[m+1, n] * (B - B[m])/(B[m+1] - B[m])$$ [Math. 16B]

$$L'[n+1] = L_{ideal}[m, n+1] * (B[m+1] - B)/(B[m+1] - B[m]) + L_{ideal}[m+1, n+1] * (B - B[m])/(B[m+1] - B[m])$$

$$L' = L'[n] * (S[n+1] - S)/(S[n+1] - S[n]) + L'[n+1] * (S - S[n])/(S[n+1] - S[n])$$

In such a manner, from bone thickness B and soft-tissue thickness S not including scattered rays set as initial values, the function H'=h(B,S) for obtaining transmittance H' including scattered rays at high energy and the function L'=l(B,S) for obtaining transmittance L' including scattered rays at low energy are generated.

Figure 13:
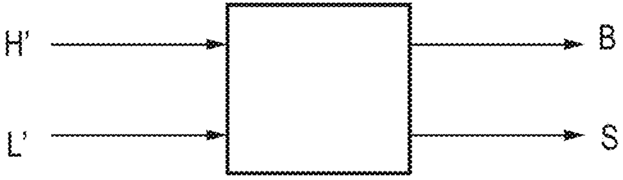
FIG. 13 is a block diagram of thickness calculation according to the embodiment.

FIG. 13 illustrates a block diagram of thickness calculation relating to the second processing in the embodiment. The block diagram in FIG. 12 described earlier is included in the block diagram in FIG. 13, and when the processing corresponding to the block diagram in FIG. 13 is executed, the processing corresponding to the block diagram in FIG. 12 is executed first, and the processing corresponding to the block diagram in FIG. 13 is executed using the results of the processing corresponding to the block diagram in FIG. 12. The processing corresponding to the block diagram in FIG. 13 is repeatedly executed until the bone thickness B and the soft tissue thickness S converge. In the processing corresponding to the block diagram in FIG. 13, the processing corresponding to the block diagram in FIG. 12 is executed with bone thickness B and soft tissue thickness S obtained in the process of repeated computation being input to the block diagram illustrated in FIG. 12, and the processing corresponding to the block diagram in FIG. 13 is repeatedly executed using the results of the processing corresponding to the block diagram in FIG. 12.

In the processing corresponding to the block diagram in FIG. 13, the signal processing unit 133 obtains bone thickness B and soft tissue thickness S not including scattered rays (with reduced scattered rays) from transmittance H' including scattered rays at high energy and transmittance L' including scattered rays at low energy. Here, the signal processing unit 133 obtains bone thickness B and soft tissue thickness S not including scattered rays (with reduced scattered rays) from transmittance H' including scattered rays and transmittance L' including scattered rays using the functions H'=h(B,S) and L'=l(B,S) obtained in the processing corresponding to the block diagram in FIG. 12.

The signal processing unit 133 can obtain the bone thickness B and the soft tissue thickness S by solving a non-linear system of equations using the Newton-Raphson method. The calculation method of the Newton-Raphson method is substantially the same as that in the signal processing in FIG. 6; however, there is a difference in that processing is performed in which the functions for obtaining transmittance (H', L') including scattered rays are used in place of the theoretical formulae of transmittance (H, L) indicated in [Math. 4]. That is, high-energy transmittance $H'^m$ after an mth iteration and low-energy transmittance $L'^m$ after the mth iteration can be expressed using, in place of [Math. 5], [Math. 17] below, where m is the number of iterations of the Newton-Raphson method, $B^m$ is the bone thickness after the mth iteration, and $S^m$ is the soft tissue thickness after the mth iteration.

$$H'^m = h(B^m, S^m)$$ [Math. 17]

$$L'^m = l(B^m, S^m)$$

Furthermore, the change rate of transmittance when there is a minute change in thickness is calculated from a difference based on the change in material thickness (amount of change) as indicated in [Math. 18] below, instead of using [Math. 6], in which the change rate is calculated by differentiation. That is, the change rate of transmittance $H'^m$ and transmittance $L'^m$ can be expressed using [Math. 18] below, where δ is a minute change in material thickness in bone thickness B and soft tissue thickness S.

$$\frac{\partial H'^m}{\partial B^m} = \frac{h(B^m + \delta, S^m) - h(B^m - \delta, S^m)}{2\delta}$$ [Math. 18]

$$\frac{\partial L'^m}{\partial B^m} = \frac{l(B^m + \delta, S^m) - l(B^m - \delta, S^m)}{2\delta}$$

$$\frac{\partial H'^m}{\partial S^m} = \frac{h(B^m, S^m + \delta) - h(B^m, S^m - \delta)}{2\delta}$$

$$\frac{\partial L'^m}{\partial S^m} = \frac{l(B^m, S^m + \delta) - l(B^m, S^m - \delta)}{2\delta}$$

Based on a change in thickness of the first material (bone thickness B) (minute change δ), the signal processing unit 133 obtains a first change rate (first formula in [Math. 18]) of the first function (function H'=h(B,S)) and a second change rate (second formula in [Math. 18]) of the second function (function L'=l(B,S)). Furthermore, based on a change in thickness of the second material (soft tissue thickness S) (minute change δ), the signal processing unit 133 obtains a third change rate (third formula in [Math. 18]) of the first function (function H'=h(B,S)) and a fourth change rate (fourth formula in [Math. 18]) of the second function (function L'=l(B,S)).

By performing the calculations from [Math. 7] to [Math. 9] using the changes rates in [Math. 18], bone thickness $B^{m+1}$ and soft tissue thickness $S^{m+1}$ after the (m+1)th iteration can be obtained in a similar manner as in FIG. 6.

In the calculations from [Math. 7] to [Math. 9], the signal processing unit 133 obtains a first difference ($H-H'^m$) between transmittance H not including scattered rays at the first radiation energy (high energy) and transmittance H' including scattered rays output from the first function (function H'=h(B,S)). Furthermore, the signal processing unit 133 obtains a second difference ($L-L'^m$) between transmittance L not including scattered rays at the second radiation energy (low energy) and transmittance L' including scattered rays output from the second function (function L'=l(B,S)).

In the calculation in [Math. 9], the signal processing unit 133 obtains a thickness image of the first material ($B'^{m+1}$) by repeatedly executing energy subtraction processing in which the fourth change rate ($\delta L'^m/\delta S^m$) and the first difference ($H-H'^m$), and the third change rate ($\delta H'^m/\delta S^m$) and the second difference ($L-L'^m$) are used. Furthermore, the signal processing unit 133 obtains a thickness image of the second material ($S^{m+1}$) by repeatedly executing energy subtraction processing in which the second change rate ($\delta L'^m/\delta B^m$) and the first difference ($H-H'^m$), and the first change rate ($\delta H'^m/\delta B^m$) and the second difference ($L-L'^m$) are used.

By repeating such calculations, the change rate of high-energy transmittance $H'^m$ and the change rate of low-energy transmittance $L'^m$ after the mth iteration converge. That is, as a result of the repetitive calculation by the signal processing unit 133, high-energy transmittance $H'^m$ including scattered rays after the mth iteration converges to transmittance H not including scattered rays, and low-energy transmittance $L'^m$ including scattered rays after the mth iteration converges to transmittance L not including scattered rays. For example, in [Math. 9], the difference between high-energy transmittance $H'^m$ including scattered rays and transmittance H not including scattered rays infinitely approaches 0. Furthermore, the difference between low-energy transmittance $L'^m$ including scattered rays and transmittance L not including scattered rays infinitely approaches 0.

The signal processing unit 133 obtains an image of first transmittance H not including scattered rays in which the scattered-ray component has been reduced from the transmittance H' including scattered rays output from the first function, and an image of second transmittance L not including scattered rays in which the scattered-ray component has been reduced from transmittance L' including scattered rays output from the second function. Furthermore, using the image of first transmittance H and the image of second transmittance L, the signal processing unit 133 obtains a thickness image of the first material and a thickness image of the second material in which the scattered-ray component has been reduced.

Specifically, as a result of repetitive computation using [Math. 18] and [Math. 7] to [Math. 9], the signal processing unit 133 obtains transmittance H not including scattered rays (image of first transmittance H) as transmittance in which the scattered-ray component has been reduced from high-energy transmittance H' including scattered rays.

Furthermore, as a result of repetitive computation using [Math. 18] and [Math. 7] to [Math. 9], the signal processing unit 133 similarly obtains transmittance L not including scattered rays (image of second transmittance L) as transmittance in which the scattered-ray component has been reduced from low-energy transmittance L' including scattered rays.

As a result of the signal processing unit 133 performing energy subtraction processing using high-energy transmittance $H'^m$ and low-energy transmittance $L'^m$ having converged in the repetitive computation, bone thickness $B^m$ after the mth iteration converges to the bone thickness B and soft tissue thickness $S^m$ after the mth iteration converges to the soft tissue thickness S. The non-linear system of equations shown in [Math. 17] can be solved in such a manner. By calculating [Math. 17] for all pixels, the bone thickness B and the soft tissue thickness S not including scattered rays (with reduced scattered rays) can be obtained from an image of high-energy transmittance H' including scattered rays and an image of low-energy transmittance L' including scattered rays.

In the present embodiment, an example has been described in which the Newton-Raphson method is used as the method for analyzing a non-linear system of equations; however, there is no limitation to this analysis example, and analysis methods based on iterative solution methods such as the least-squares method and the bisection method may be used. Furthermore, various modifications can be adopted in regard to the configuration of using the generation of tables illustrated in FIG. 7 and the referencing of tables illustrated in FIG. 8 to allow energy subtraction signal processing to be performed with high accuracy and at high speed, and increase calculation speed.

Furthermore, in the present embodiment, an example has been described in which bone thickness B and soft tissue thickness S not including scattered rays are obtained from an image of transmittance H' including scattered rays at high energy and an image of transmittance L' including scattered rays at low energy. However, the present embodiment is not limited to this example, and, for example, scattered ray correction may be performed by using the tables for scattered ray correction illustrated in FIG. 11, in which two materials are taken into consideration, to obtain transmittance H not including scattered rays at high energy and transmittance L not including scattered rays at low energy from transmittance H' including scattered rays at high energy and transmittance L' including scattered rays at low energy, etc.

Furthermore, for the sake of convenience, no specific limitation is set in the present embodiment in regard to the arrangement positions of flat plates when tables for scattered ray correction in which two materials are taken into consideration are created. However, the technique disclosed herein is not limited to this example, and tables for scattered ray correction may be created by performing measurement in a state in which the arrangement positions of the flat plates are specifically set. For example, the distance (OID) between an object (for example, a flat plate) and the two-dimensional detector 106 in the X-ray imaging apparatus 104 may be measured, and a table for scattered ray correction may be created for each distance (OID). When the distance (OID) between the two-dimensional detector 106 and an object (for example, a flat plate) changes, the scattered ray dose may also change; thus, the table for scattered ray correction to be used can be changed in accordance with the distance (OID). Furthermore, the scattered ray dose can be calculated by performing interpolation using tables for scattered ray correction at a plurality of distances (OID). Thus, correction processing can be performed by calculating the scattered ray dose with higher accuracy in accordance with arrangement position of a flat plate. For example, information regarding transmittance obtained for each of multiple distances between an object and the two-dimensional detector 106 for detecting radiation is stored in the storage unit 136. By using information (information regarding transmittance) obtained by performing interpolation based on the distance of an object during imaging, the signal processing unit 133 may obtain information regarding transmittance that corresponds to a thickness of the predetermined material or transmittance corresponding to a combination of a thickness of the first material and a thickness of the second material.

Note that, in the present embodiment, an indirect-type X-ray sensor in which a phosphor is used was adopted as the X-ray imaging apparatus 104. However, the technique disclosed herein is not limited to such an embodiment. For example, a direct-type X-ray sensor in which a direct conversion material such as CdTe is used may be adopted.

Furthermore, in the present embodiment, the tube voltage of the X-ray generation apparatus 101 was changed. However, the technique disclosed herein is not limited to such an embodiment. The energy of the X-rays to which the X-ray imaging apparatus 104 is exposed may be changed by temporally switching filters of the X-ray generation apparatus 101.

Furthermore, in the present embodiment, images at different energies were obtained by changing the X-ray energy. However, the technique disclosed herein is not limited to such an embodiment. By adopting a stacked configuration in which a plurality of phosphors 105 and two-dimensional detectors 106 are stacked, images at different energies may be obtained from the two-dimensional detector on the front side and the two-dimensional detector on the rear side with respect to the direction of incidence of X-rays. The two-dimensional detector 106 is not limited to that for medical use, and may be a two-dimensional detector for industrial use.

Furthermore, in the present embodiment, energy subtraction processing is performed using the imaging control apparatus 103 of the radiation imaging system. However, the technique disclosed herein is not limited to such an embodiment. Images obtained by the imaging control apparatus 103 may be transferred to a different computer to perform energy subtraction processing. For example, a configuration may be adopted in which obtained images are transferred to a different image processing apparatus (image viewer) via a medical PACS and displayed after energy subtraction processing is performed.

The technique disclosed herein allows the thickness of materials to be obtained accurately.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2023-107226, filed Jun. 29, 2023, which is hereby incorporated by reference herein in its entirety.

What is claimed is:

1. An image processing apparatus, comprising:

a processing unit configured to obtain thickness images of first and second materials in which scattered rays have been corrected using a plurality of pieces of information that correspond to a plurality of mutually different radiation energies and that have been obtained by irradiating an object with radiation and performing imaging, and information regarding transmittance including scattered rays and transmittance not including the scattered rays that is set in advance for each of multiple thicknesses of a first material and a second material that is different from the first material; and a storage unit configured to store information regarding the transmittance obtained for each of multiple thicknesses of a predetermined material for each of a first radiation energy and a second radiation energy that is different from the first radiation energy;

the processing unit being configured to obtain information regarding transmittance that corresponds to a thickness of the predetermined material by performing correction of the information stored in the storage unit, the information regarding transmittance including the scattered rays obtained for each combination of a thickness of the first material and a thickness of the second material is stored in the storage unit; and the processing unit being configured to obtain information regarding transmittance including the scattered rays for the combination by performing correction of the information obtained from the storage unit based on the combination, wherein when the scattered rays are not included in the first radiation energy, the processing unit is configured to generate a first function that outputs information regarding transmittance from a combination of a thickness of the first material and a thickness of the second material including the scattered rays for the combination, when the scattered rays are not included in the second radiation energy, the processing unit is configured to generate a second function that outputs information regarding transmittance from a combination of a thickness of the first material and a thickness of the second material including the scattered rays for the combination, and the processing unit is configured to obtain a first change rate of the first function and a second change rate of the second function based on a change in thickness of the first material, and to obtain a third change rate of the first function and a fourth change rate of the second function based on a change in thickness of the second material.

2. The image processing apparatus according to claim 1, wherein information that corresponds to a first radiation energy includes a first radiation image among the plurality of radiation energies, and information that corresponds to a second radiation energy includes a second radiation image, among the plurality of radiation energies that is different from the first radiation energy.

3. The image processing apparatus according to claim 2, wherein the first radiation image includes data in which signal values of electric signals obtained by the imaging and position information indicating a two-dimensional array of the signal values are associated with one another, and the second radiation image includes data in which signal values of electric signals obtained by the imaging and position information indicating a two-dimensional array of the signal values are associated with one another.

4. The image processing apparatus according to claim 1, wherein the processing unit is configured to obtain information regarding transmittance including the scattered rays at the first radiation energy and information regarding transmittance including the scattered rays at the second radiation energy as a result of the correction.

5. The image processing apparatus according to claim 1, wherein the processing unit is configured to obtain a first difference between transmittance not including the scattered rays at the first radiation energy and transmittance including the scattered rays output from the first function, and is configured to obtain a second difference between transmittance not including the scattered rays at the second radiation energy and transmittance including the scattered rays output from the second function.

6. The image processing apparatus according to claim 5, wherein the processing unit is configured to obtain the thickness image of the first material by repeatedly executing energy subtraction processing in which the fourth change rate and the first difference, and the third change rate and the second difference are used, and is configured to obtain the thickness image of the second material by repeatedly executing energy subtraction processing in which the second change rate and the first difference, and the first change rate and the second difference are used.

7. The image processing apparatus according to claim 6, wherein the processing unit is configured to obtain an image of first transmittance not including the scattered rays in which a scattered-ray component has been reduced from the transmittance including the scattered rays output from the first function, and is configured to obtain an image of second transmittance not including the scattered rays in which a scattered-ray component has been reduced from the transmittance including scattered rays output from the second function, and is configured to obtain the thickness image of the first material and the thickness image of the second material in which the scattered-ray component has been reduced using the image of the first transmittance and the image of the second transmittance.

8. The image processing apparatus according to claim 1, wherein the processing unit is configured to obtain transmittance not including the scattered rays that corresponds to the thickness of the predetermined material by performing correction in which transmittance including the scattered rays and transmittance not including the scattered rays stored in the storage unit are used.

9. The image processing apparatus according to claim 8, wherein the storage unit is configured to store a ratio between a scattered-ray component included in the radiation and a primary-radiation component corresponding to the radiation directly reaching a two-dimensional detector from a radiation source for each of multiple thicknesses of the predetermined material, and the processing unit is configured to obtain the transmittance not including the scattered rays that corresponds to the thickness of the predetermined material by performing correction in which the ratio and transmittance including the scattered rays are used.

10. The image processing apparatus according to claim 8, wherein the storage unit is configured to store a difference between transmittance including the scattered rays and transmittance not including the scattered rays for each of multiple thicknesses of the predetermined material, and the processing unit is configured to obtain the transmittance not including the scattered rays that corresponds to the thickness of the predetermined material by performing correction in which the difference and transmittance including the scattered rays are used.

11. The image processing apparatus according to claim 1, wherein the storage unit is configured to store information regarding the transmittance obtained for each of multiple distances between the object and a two-dimensional detector for detecting the radiation, and the processing unit is configured to obtain the information regarding transmittance that corresponds to the thickness of the predetermined material using the information obtained by performing interpolation based on the distance of the object during imaging.

12. The image processing apparatus according to claim 1, wherein the thickness image of the first material is a bone image, and the thickness image of the second material is a soft tissue image.

13. A radiation imaging system, comprising:

a radiation imaging apparatus including a two-dimensional detector; and the image processing apparatus according to claim 1, the image processing apparatus being configured to obtain images in which scattered rays included in radiation detected by the two-dimensional detector have been corrected.

14. An image processing method, comprising:

obtaining thickness images of first and second materials in which scattered rays have been corrected using a plurality of pieces of information that correspond to a plurality of mutually different radiation energies and that have been obtained by irradiating an object with radiation and performing imaging, and information regarding transmittance including scattered rays and transmittance not including the scattered rays that is set in advance for each of multiple thicknesses of a first material and a second material that is different from the first material;

storing information regarding the transmittance obtained for each of multiple thicknesses of a predetermined material for each of a first radiation energy and a second radiation energy that is different from the first radiation energy; and obtaining information regarding transmittance that corresponds to a thickness of the predetermined material by performing correction of the stored information, the information regarding transmittance including the scattered rays obtained for each combination of a thickness of the first material and a thickness of the second material, wherein obtaining information regarding transmittance by performing correction of the information obtained from the storage unit based on the combination, including the scattered rays for the combination, when the scattered rays are not included in the first radiation energy, generating a first function that outputs information regarding transmittance including the scattered rays for the combination, from a combination of a thickness of the first material and a thickness of the second material, when the scattered rays are not included in the second radiation energy, generating a second function that outputs information regarding transmittance including the scattered rays for the combination, from a combination of a thickness of the first material and a thickness of the second material, and obtaining a first change rate of the first function and a second change rate of the second function based on a change in thickness of the first material, and obtaining a third change rate of the first function and a fourth change rate of the second function based on a change in thickness of the second material.

15. A non-transitory storage medium in which is stored a program that causes a computer to execute the image processing method according to claim 14.

* * * * *